(12) United States Patent
Bhimavarapu et al.

(10) Patent No.: US 11,410,771 B2
(45) Date of Patent: Aug. 9, 2022

(54) PATIENT CARE DEVICES WITH OPEN COMMUNICATION

(71) Applicant: Stryker Corporation, Kalamazoo, MI (US)

(72) Inventors: Krishna Sandeep Bhimavarapu, Kalamazoo, MI (US); Joshua Elmer Mix, Portage, MI (US); Richard A. Derenne, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/996,037

(22) Filed: Jun. 1, 2018

(65) Prior Publication Data

US 2018/0350464 A1     Dec. 6, 2018

Related U.S. Application Data

(60) Provisional application No. 62/513,641, filed on Jun. 1, 2017.

(51) Int. Cl.
*G16H 40/63* (2018.01)
*G06F 9/451* (2018.01)
(Continued)

(52) U.S. Cl.
CPC ............. *G16H 40/63* (2018.01); *A61G 7/018* (2013.01); *A61G 7/05* (2013.01); *G06F 9/4411* (2013.01);
(Continued)

(58) Field of Classification Search
CPC ........ G16H 40/63; G16H 40/67; G06F 9/451; G06F 9/4411; A61G 7/05; A61G 2203/32; A61G 7/012; A61G 7/015; A61G 7/018
See application file for complete search history.

(56) References Cited

U.S. PATENT DOCUMENTS 5,713,856 A    2/1998    Eggers et al.
5,843,007 A    12/1998   McEwen et al.
(Continued)

FOREIGN PATENT DOCUMENTS

GB    2214678 A    9/1989

OTHER PUBLICATIONS

Stryker Operations Manual InTouch Critical Care Bed Model FL27, Apr. 2014.

*Primary Examiner* — Nathan L Laughlin
(74) *Attorney, Agent, or Firm* — Warner Norcross + Judd LLP

(57) ABSTRACT

Patient care devices, including beds, cots, stretchers, recliners, chairs, thermal control systems, and IV poles, include a user interface for controlling an aspect of the patient care device, a port for communicating with an external device, and a control system. The control system determines when an external device is communicating with the port, what type of device the external device is, and if the patient care device includes software for allowing the user interface to act as a user interface of the external device. In some embodiments, the control system receives a device type identifier when an external device is coupled to the port, selects a software module for communicating with the coupled external device, and uses the selected software module for communicating with the coupled external device. Multiple external devices may be connected to the port and display data on a display of the patient care device.

17 Claims, 10 Drawing Sheets

(51) Int. Cl.
 *A61G 7/05* (2006.01)
 *G06F 9/4401* (2018.01)
 *A61G 7/018* (2006.01)
 *G16H 40/67* (2018.01)
 *A61G 7/012* (2006.01)
 *A61G 7/015* (2006.01)

(52) U.S. Cl.
 CPC ............. *G06F 9/451* (2018.02); *G16H 40/67* (2018.01); *A61G 7/012* (2013.01); *A61G 7/015* (2013.01); *A61G 2203/32* (2013.01)

(56) References Cited

U.S. PATENT DOCUMENTS

| | | | |
|---|---|---|---|
| 6,231,532 B1 | 5/2001 | Watson et al. | |
| 6,387,065 B1 | 5/2002 | Tumey | |
| 6,440,093 B1 | 8/2002 | McEwen et al. | |
| 6,544,202 B2 | 4/2003 | McEwen et al. | |
| 6,735,799 B1 | 5/2004 | Ellis et al. | |
| 6,736,787 B1 | 5/2004 | McEwen et al. | |
| 6,829,796 B2 | 12/2004 | Salvatini et al. | |
| 6,884,255 B1 | 4/2005 | Newton | |
| 6,988,423 B2 | 1/2006 | Bolam et al. | |
| 7,017,208 B2 | 3/2006 | Weismiller et al. | |
| 7,076,993 B2 | 7/2006 | Cook | |
| 7,256,771 B2 | 8/2007 | Novak et al. | |
| 7,354,410 B2 | 4/2008 | Perry et al. | |
| 7,398,803 B2 | 7/2008 | Newton | |
| 7,490,620 B2 | 2/2009 | Tesluk et al. | |
| 7,591,796 B1 | 9/2009 | Barak et al. | |
| 7,641,623 B2 | 1/2010 | Biondo et al. | |
| 7,741,966 B2 | 6/2010 | Bonnefin et al. | |
| 7,904,976 B2 | 3/2011 | Hakamiun et al. | |
| 7,909,786 B2 | 3/2011 | Bonnefin et al. | |
| 8,235,922 B2 | 8/2012 | Rowe et al. | |
| 8,256,459 B2 | 9/2012 | Tesluk et al. | |
| 8,257,287 B2 | 9/2012 | Hanlon et al. | |
| 8,506,507 B2 | 8/2013 | Bock | |
| 8,562,600 B2 | 10/2013 | Kirkpatrick et al. | |
| 8,583,728 B2 | 11/2013 | Irwin et al. | |
| 8,660,853 B2 | 2/2014 | Robb et al. | |
| 8,845,562 B2 | 9/2014 | Receveur et al. | |
| 9,253,259 B2 | 2/2016 | Tallent et al. | |
| 9,430,723 B1 * | 8/2016 | Panda | G06F 3/12 |
| 9,465,915 B2 | 10/2016 | McNeely et al. | |
| 9,642,759 B2 | 5/2017 | Stryker et al. | |
| 2003/0052787 A1 | 3/2003 | Zerhusen et al. | |
| 2005/0063575 A1 | 3/2005 | Ma et al. | |
| 2007/0276901 A1 | 11/2007 | Glinsky et al. | |
| 2009/0217080 A1 * | 8/2009 | Ferguson | G08B 7/06 714/4.1 |
| 2009/0312823 A1 * | 12/2009 | Patience | A61F 7/007 607/104 |
| 2010/0076356 A1 | 3/2010 | Biondo et al. | |
| 2010/0249540 A1 * | 9/2010 | Lisogurski | G16H 40/20 600/301 |
| 2011/0181394 A1 * | 7/2011 | Blair | A61B 5/062 340/10.1 |
| 2013/0014324 A1 | 1/2013 | Receveur et al. | |
| 2013/0231596 A1 | 9/2013 | Hornbach et al. | |
| 2013/0331748 A1 | 12/2013 | Wright et al. | |
| 2014/0031730 A1 | 1/2014 | Hornbach et al. | |
| 2014/0058301 A1 | 2/2014 | Mros et al. | |
| 2014/0094726 A1 | 4/2014 | Malhi et al. | |
| 2014/0207036 A1 | 7/2014 | Perry et al. | |
| 2015/0000035 A1 * | 1/2015 | Becker | A61B 5/1117 5/11 |
| 2015/0033295 A1 | 1/2015 | Huster | |
| 2015/0094623 A1 | 4/2015 | Howell et al. | |
| 2016/0140307 A1 * | 5/2016 | Brosnan | G16H 40/67 600/324 |
| 2016/0367420 A1 | 12/2016 | Zerhusen et al. | |
| 2018/0036544 A1 * | 2/2018 | Delisle | A61N 1/046 |
| 2018/0213944 A1 * | 8/2018 | Bedel | A61G 5/10 |
| 2018/0311012 A1 * | 11/2018 | Moctezuma | G06K 9/4628 |

* cited by examiner

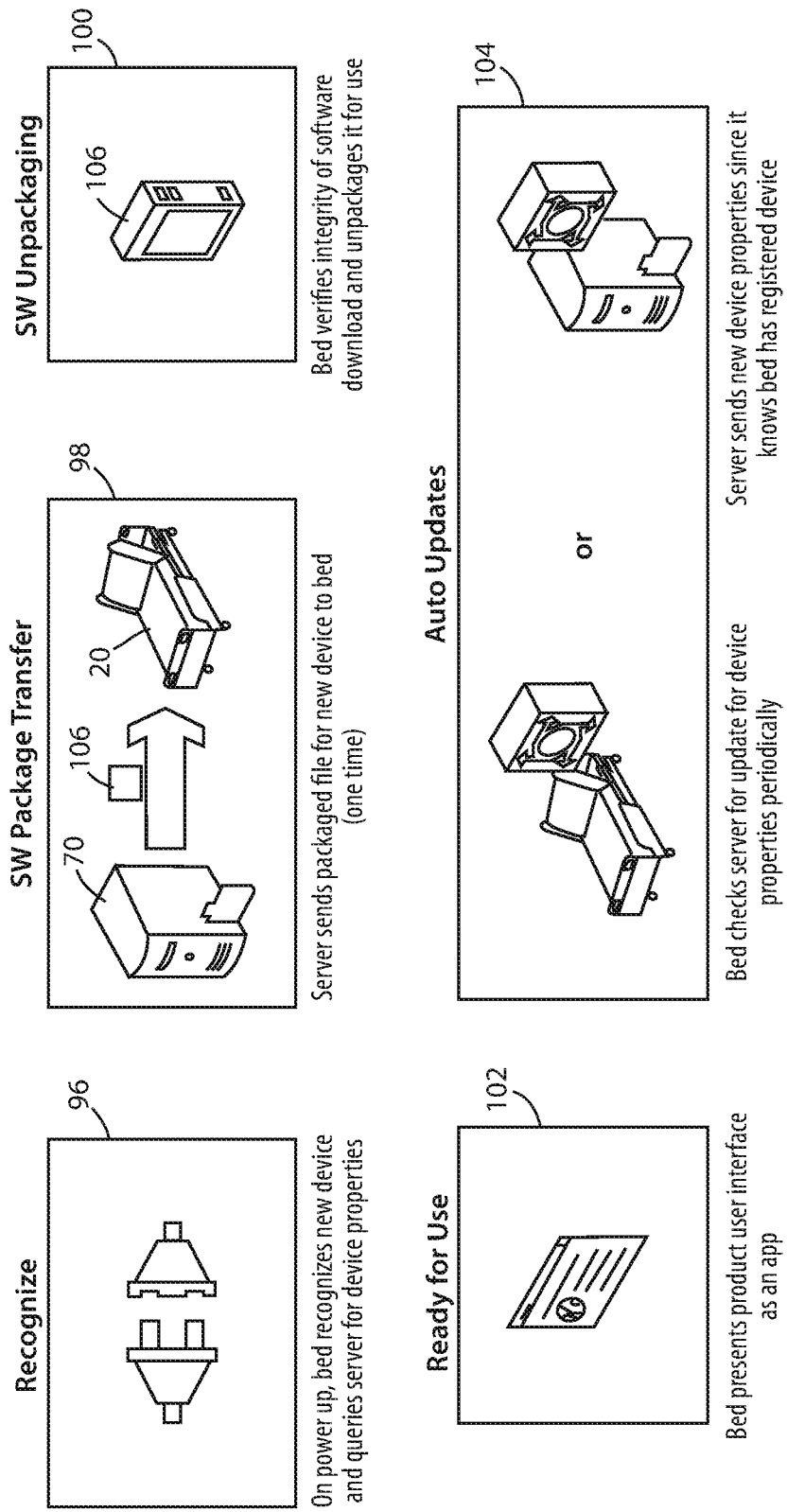

| Device 60 | Feature | Units | User Interface 50 Function |
|---|---|---|---|
| chair | battery power | % (milliamp-hours) and level (L,M, or H) | display |
| | patient controls lock | on or off | display and control |
| | brake | on or off | display |
| | seat height | inches | display |
| | footrest angle | degrees | display |
| | seat angle | degrees | display |
| | Fowler angle | degrees | display |
| | exit alarm | alert level and duration | display and control |
| incontinence detector | alert | alert level and duration | display and control |
| | wet or not | level of wetness | display |
| camera | face recognition | identification (text) | display and control |
| | gesture recognition | patient activity | display and control |
| | | caregiver activity | display and control |
| | auto document | confirmation (Y or N) | display and control |
| | object detection | name of object | display and control |
| | | condition of object | display and control |
| | protocol detection | patient activity | display and control |
| | | caregiver activity | display and control |
| interface pressure sensor | pressure map | color of pressure | display |
| | | mmHg per cell | display |
| | | map | display |
| | alerts | alert level and duration | display and control |
| | timer | time | display and control |
| | turn detection | left, right, left partial, right partial | display |
| microphone | recommended noise | dB level | display |
| | ambient room noise | dB level | display |
| DVT pump | error | low, high, etc. | display |
| | pressure | mmHg (40-100) | display and control |
| | duration | time ON and time OFF | display and control |
| | hold time | time ON and time OFF | display and control |
| | leg | one or two | display and control |
| vibration therapy | duration | time (ON and OFF) | display and control |
| | frequency | Hertz | display and control |
| | amplitude | intensity (0 to 10) | display and control |
| temperature management device | battery life | % (milliamp-hours) and level (L,M, or H) | display |
| | safety temp (1,2) | temperature | display |
| | fan speed | % (flow) and level (L, M, or H) | display |
| | flow of water (port 1,2,3) | liters per minute | display |
| | water temp | degrees | display |
| | target patient temperature | degrees | display |
| | measured patient temperature | degrees | display |
| vital signs | repiration rate | breaths per minute | display |
| | continuous non-invasive BP | Low/High mmHg | display |
| | pulse Ox | %SpO2 | display |
| | end tidal CO2 | mmHg | display |
| | patient body temperature | degrees | display |
| | patient core body temperature | degrees | display |
| | heart rate with ECG | waveform | display |
| | heart rate | beats per minute | display |

FIG. 12

| Device 60 (142) | Feature (144) | Units (146) | User Interface 50 Function (148) |
|---|---|---|---|
| patient support apparatus | reverse Trendelenberg | yes or no | display |
| | Trendelenberg | yes or no | display |
| | supine | yes or no | display |
| | chair | yes or no | display |
| | Fowler angle | degrees | display |
| | propulsion system | speed and direction | display |
| | | on or off | display |
| | scale last zeroed | date | display |
| | weight | pounds or kilograms | display |
| | location | room #, hallway, etc. | display |

FIG. 14

PATIENT CARE DEVICES WITH OPEN COMMUNICATION

CROSS-REFERENCE TO RELATED APPLICATIONS

This application claims priority to U.S. provisional patent application Ser. No. 62/513,641 filed Jun. 1, 2017, by inventors Krishna Bhimavarapu et al. and entitled PATIENT CARE DEVICES WITH OPEN COMMUNICATION, the complete disclosure of which is incorporated herein by reference.

BACKGROUND

The present disclosure relates to patient care devices, such as patient support apparatuses (e.g. beds, stretchers, chairs, recliners, operating tables, cots, etc.), thermal control units adapted to control a patient's temperature, computerized medical device stands, such as IV poles, and other types of medical devices.

Most of the aforementioned patient care devices include a user interface adapted to allow a user to operate one or more aspects of the patient care device. However, not all medical devices used in the treatment and/or evaluation of a patient include such a user interface, or include a user interface that is easy to use by a user.

SUMMARY

Patient care devices according to one or more aspects of the present disclosure include user interfaces that are able to be shared with one or more external devices, thereby enabling the one or more external devices to share the screen space of a display on the patient care device's user interface, and/or allow the external device to be at least partially controlled by one or more controls positioned on the patient care device. In some embodiments, the patient care device is adapted to automatically download and/or update one or more drivers and/or other software for allowing the user interface of the patient care device to act as a proxy user interface for one or more external devices. This enables the medical device to be controlled and/or have its data displayed, even if the medical device does not itself include a user interface. Alternatively, or additionally, this allows a standardized and single user interface to be used for controlling multiple devices (e.g. the patient care device and one or more external devices). Software updates may be carried out automatically by the patient care device to ensure it has the latest version of software for sharing its user interface with the one or more external devices.

According to one embodiment of the present disclosure, a patient support apparatus is provided that includes a support surface, a user interface, a port, and a control system. The support surface is adapted to support a patient. The user interface includes a control for controlling movement of a component of the patient support apparatus. The port is for communicating with an external device. The control system determines when an external device is communicating with the port, what type of device the external device is, and if the patient support apparatus includes software stored in a memory of the patient support apparatus for allowing the user interface to act as a user interface for the external device.

According to other aspects, the port may be a Universal Serial Bus (USB) port, another type of wired port, or a wireless port.

In some embodiments, the patient support apparatus further includes a transceiver adapted to allow the control system to communicate with a network of a healthcare facility. If the software is not stored in the memory of the patient support apparatus, the control system is configured to automatically request the software from a server on the network of the healthcare facility using the transceiver. Alternatively, or additionally, if the software is not stored in the memory of the patient support apparatus, the control system is configured to automatically request the software from the external device itself.

The control system is further adapted in some embodiments to receive a software version identifier from the external device and automatically check to see if a later version exists for the external device by communicating with a server on a network of a healthcare facility. If a later version does exist, the control system automatically downloads the later version from the server.

The control system allows the patient support apparatus user interface to act as a user interface for the external device by performing one or both of the following tasks: displaying data from the external device on a display of the user interface, and allowing the patient support apparatus user interface to act as a user interface for the external device by allowing an aspect of the external device to be controlled via a control of the patient support apparatus user interface.

The external device is selected from the following group, in some embodiments: an electrical muscle stimulation device; a chair; a stretcher; a patient temperature management device adapted to control a temperature of the patient; a pressure mapping device adapted to detect interface pressure between the patient and the support surface; a voice-over-IP (VoIP) device adapted to allow the patient to aurally communicate with a person located remote from the patient support apparatus; a risk assessment device adapted to assess a risk factor for the patient; a camera; a microphone; a Deep Vein Thrombosis (DVT) pump; a vital sign sensor adapted to detect a vital sign of the patient; and an incontinence detection device.

The user interface may include a touchscreen. When so included, the software includes a menu icon that, when selected, displays data on the touchscreen generated from the external device.

According to another embodiment of the present disclosure, a patient support apparatus is provided that includes a support surface, a user interface, a port, and a control system. The support surface is adapted to support a patient thereon. The user interface includes a control for controlling movement of a component of the patient support apparatus. The port allows communication between the patient support apparatus and a plurality of different types of external devices. The control system communicates with the user interface and the port and is adapted to receive a device type identifier when an external device is coupled to the port. The control system selects a software module from amongst a plurality of software modules and uses the selected software module for communicating with the coupled external device.

According to other aspects, the selected software module allows the patient support apparatus user interface to act as a user interface for the external device.

When selecting the software module, the control system communicates with a server on a network of a healthcare facility, in some embodiments.

The selected software module may be transferred to a memory of the patient support apparatus from a location off-board the patient support apparatus.

According to another aspect of the present disclosure, a patient support apparatus is provided that includes a support surface adapted to support a patient, a user interface, first and second ports, and a control system. The user interface includes a display and a control for controlling movement of a component of the patient support apparatus. The first and second ports enable communication with first and second external devices, respectively. The control system displays first and second icons on the display when the first and second external devices are coupled to the first and second ports, respectively. When the first icon is selected, the control system displays first data from the first external device on the display. When the second icon is selected, the control system displays second data from the second external device on the display.

The first and/or second device is manufactured by an entity different from a manufacturer of the patient support apparatus, in at least one embodiment.

In some embodiments, the control system automatically determines—at the time when the first external device is initially coupled to the first port—if a first piece of software is stored in a memory of the patient support apparatus for allowing the display to display the first data. If the first software is not stored in the memory of the patient support apparatus, the control system is configured to automatically request the first software from a server on the network of the healthcare facility. If the first software is stored in the memory of the patient support apparatus, the control system automatically checks to see if a later version exists for the first software by communicating with the server. If a later version exists, the control system automatically downloads the later version from the server.

In any of the embodiments disclosed herein, the patient support apparatus may further include a base, a pair of lifts coupled to the base and adapted to change a height of the support surface, and one or more siderails moveable between raised and lowered positions.

Before the embodiments of the disclosure are explained in detail, it is to be understood that the disclosure is not limited to the details of operation or to the details of construction and the arrangement of the components set forth in the following description or illustrated in the drawings. The disclosure may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the disclosure to any specific order or number of components. Nor should the use of enumeration be construed as excluding from the scope of the disclosure any additional steps or components that might be combined with or into the enumerated steps or components.

BRIEF DESCRIPTION OF THE DRAWINGS

FIG. 5 is a block diagram of a method for installing software on the patient support apparatus for communicating with an external device;

FIG. 12 is a table of exemplary external devices and their associated properties that may be coupled to the patient support apparatus to utilize the display and/or controls of the patient support apparatus;

FIG. 14 is a table of patient support apparatus properties that may be coupled to an IV tower, or other external structure, to utilize the display and/or controls of the IV tower, or other structure.

DETAILED DESCRIPTION OF THE EMBODIMENTS

Figure 1:
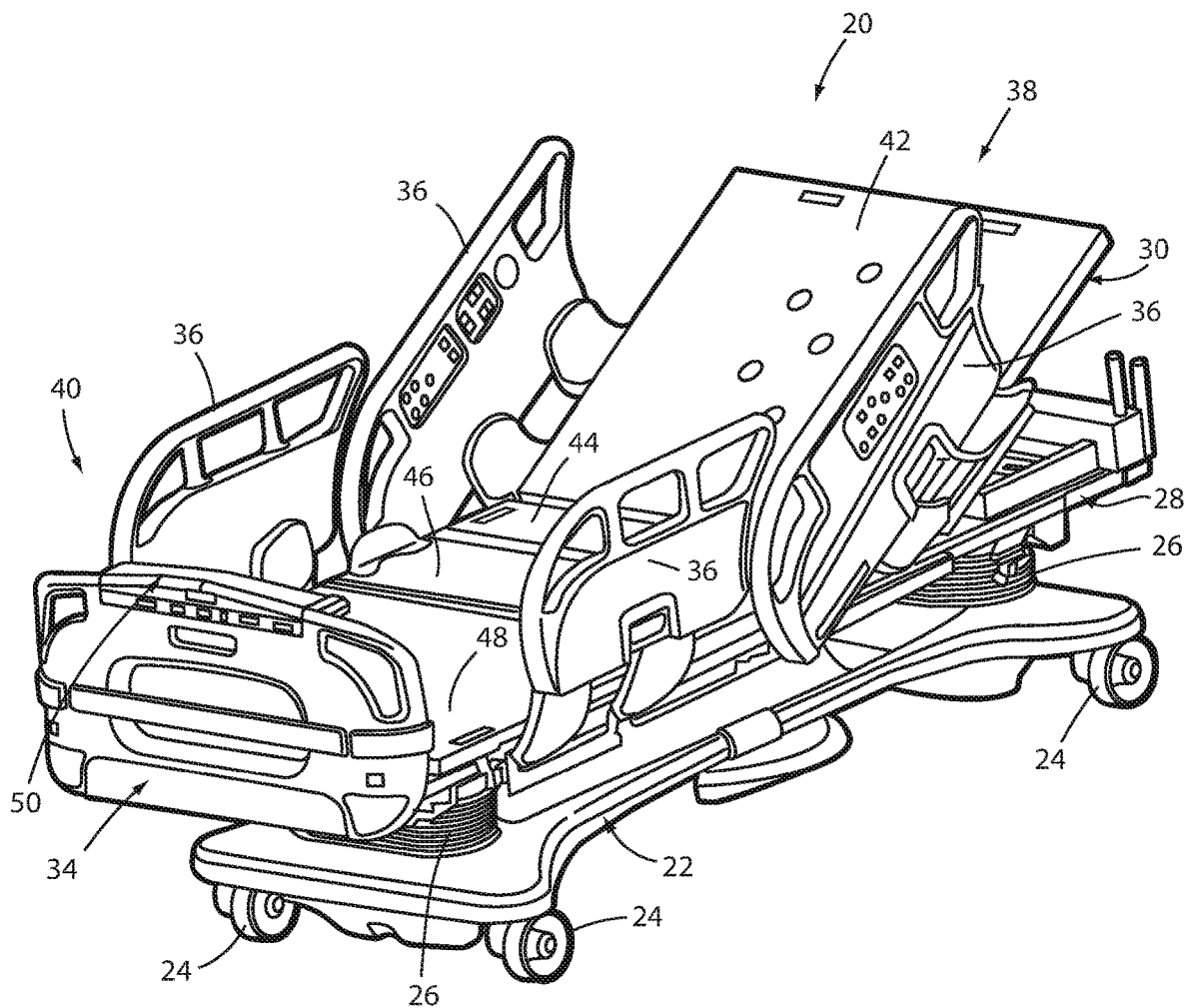
FIG. 1 is a perspective view of one example of a patient support apparatus according to one embodiment of the present disclosure.

FIG. 1 illustrates a patient support apparatus 20 that includes an improved communications and control system according to one embodiment. Although the particular form of patient support apparatus 20 illustrated in FIG. 1 is a bed adapted for use in a hospital or other medical setting, it will be understood that patient support apparatus 20 could, in different embodiments, be a cot, a stretcher, a gurney, a recliner, an operating table, a residential bed, or any other structure capable of supporting a person, whether stationary or mobile and/or whether medical or residential. Further, it will be understood that the control system principles described herein are applicable to other patient care devices besides patient support apparatuses, as will be described more below.

In general, patient support apparatus 20 includes a base 22 having a plurality of wheels 24, a pair of lifts 26 supported on the base, a litter frame 28 supported on the lifts 26, and a support deck 30 supported on the litter frame 28. Patient support apparatus 20 further includes a headboard (not shown), a footboard 34, and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, pneumatic actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard, footboard 34, and siderails 36. Support deck 30 provides a support surface for a mattress (not shown in FIG. 1), or other soft cushion, so that a person may lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Litter frame 28 is supported by two lift header assemblies (not shown) positioned on top of lifts 26. Each lift header assembly includes a pair of force sensors, which may be load cells, or other types of force sensors, such as, but not limited to, linear variable displacement transducers and/or any one or more capacitive, inductive, and/or resistive transducers that are configured to produce a changing output in response to changes in the force exerted against them. The force sensors are adapted to detect the weight of not only those components of patient support apparatus 20 that are supported by litter frame 28 (including litter frame 28 itself), but also any objects or persons who are wholly or partially being supported by support deck 30. As will be discussed in greater detail below, these force sensors may be part of an exit detection system and/or a scale system of patient support apparatus 20.

The mechanical construction of those aspects of patient support apparatus 20 not explicitly discussed herein may be implemented in the same or similar manner as they are mechanically implemented in the Model 3002 S3 bed manufactured and sold by Stryker Corporation of Kalamazoo, Mich. This mechanical construction of the Model 3002 S3 bed is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that patient support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on forms different from what is disclosed in the aforementioned references.

Patient support apparatuses 20 may also or alternatively be implemented as stretchers, cots, recliners, non-reclining chairs, operating tables, or in other manners. When implemented as a stretcher or cot, patient support apparatuses 20 may be constructed in any of the manners disclosed in commonly assigned U.S. Pat. No. 8,051,511 issued to Nahavandi et al. on Nov. 8, 2011 and entitled EMERGENCY STRETCHER; or commonly assigned U.S. Pat. No. 5,537,700 issued to Way et al. on Jul. 23, 1996 and entitled EMERGENCY STRETCHER WITH X-FRAME SUPPORT, the complete disclosures of both of which are hereby incorporated by reference herein. When patient support apparatus 20 is implemented as a recliner, it may be constructed in any of the manners disclosed in commonly assigned U.S. patent application Ser. No. 14/212,253 filed Mar. 14, 2014 by inventors Christopher Hough et al. and entitled MEDICAL SUPPORT APPARATUS, the complete disclosure of which is also incorporated herein by reference. Still other constructions of patient support apparatuses 20 may be used when one or more of the patient support apparatuses 20 are implemented as cots, stretchers, and/or recliners.

Patient support apparatus 20 further includes a user interface 50 that enables a user of patient support apparatus 20 to control one or more aspects of patient support apparatus 20. The controllable aspects include the up/down movement of litter frame 28, the pivoting of various of the deck sections 42-48, the activation and deactivation of a brake of patient support apparatus 20, the arming and disarming of an exit detection subsystem incorporated into patient support apparatus 20, and/or one or more lockouts that lock out selected controls of the occupant user interfaces positioned on the inside of the head end siderails 36.

User interface 50 is implemented in the embodiment shown in FIG. 1 as a control panel having a lid (flipped down in FIG. 1) underneath which is positioned a plurality of controls. The controls may be implemented as buttons, dials, switches, or other devices. User interface 50 also includes a display 32 (FIG. 2) for displaying information regarding patient support apparatus 20. The display is a touchscreen in some embodiments. Although FIG. 1 illustrates user interface 50 mounted to footboard 34, it will be understood that user interface 50 can be positioned elsewhere.

Figure 2:
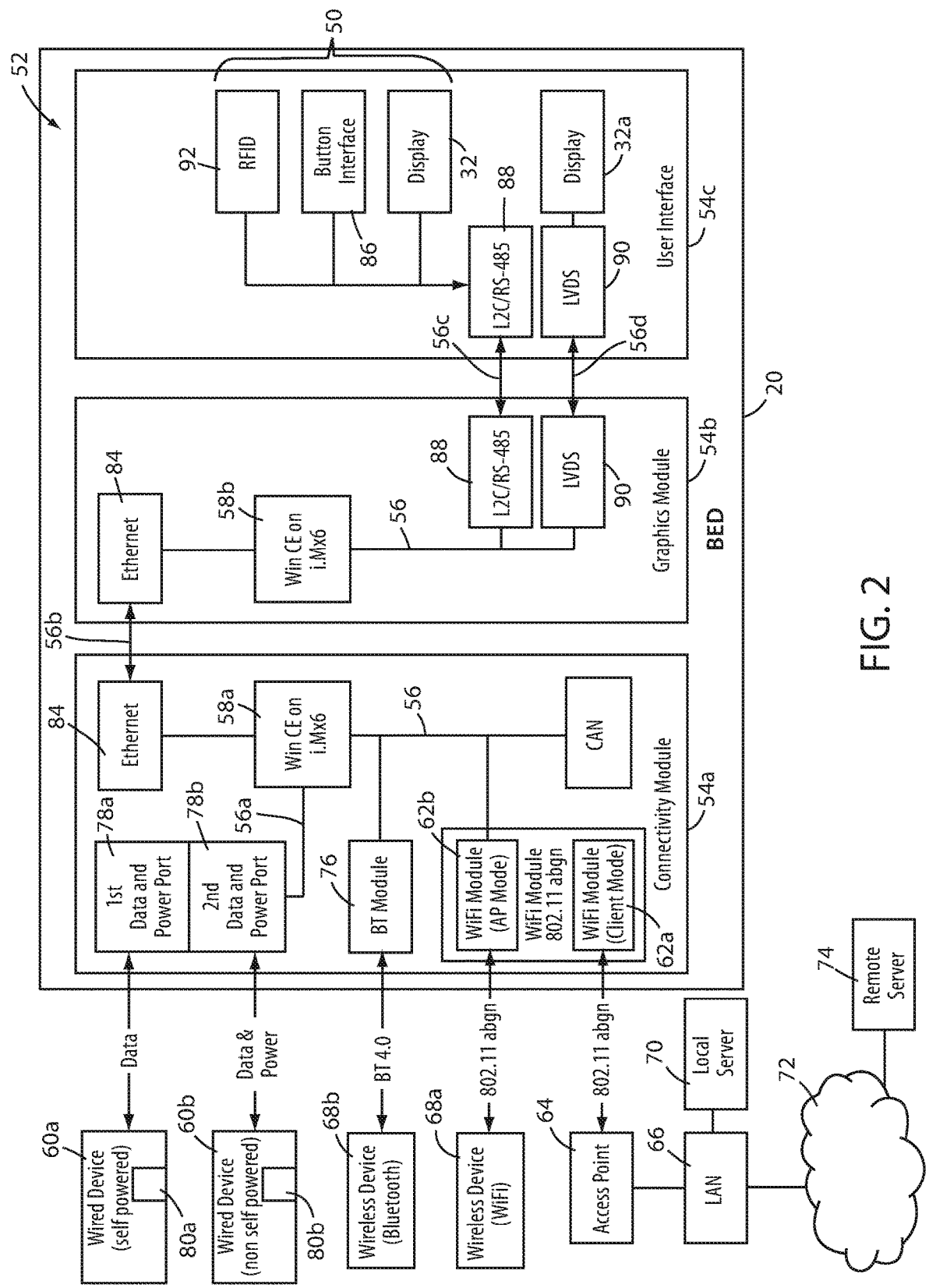
FIG. 2 is a block diagram of an illustrative control system incorporated into the patient support apparatus of FIG. 1.

FIG. 2 illustrates one example of a control system 52 for patient support apparatus 20. Control system 52 includes a plurality of nodes 54 positioned on board patient support apparatus 20. Each of the nodes 54 is coupled to one or more other nodes and/or other electronic structures by a communication medium 56. Each of the nodes 54 performs specific functions that are described in more detail below.

Although FIG. 2 illustrates a specific architecture of control system 52 having a specific number of nodes 54 connected together in a specific way by various communication media 56, it will be understood that this particular architecture is only illustrative, and that control system 52 can be varied in terms of the number of nodes 54, their function, their connections to each other, and/or the communication media 56 used to couple the nodes 54 together.

In some modified embodiments, patient support apparatus 20 includes any one or more of the additional nodes disclosed in commonly assigned U.S. patent application Ser.

No. 62/464,565, filed Feb. 28, 2017, by inventors Krishna Bhimavarapu et al. and entitled PATIENT CARE DEVICES WITH ON-BOARD NETWORK COMMUNICATION, the complete disclosure of which is incorporated herein by reference. Such additional nodes include, but are not limited to, a motion control node that controls the motors of patient support apparatus 20 and other functions of the patient support apparatus, a scale node that controls a scale and/or exit detection system integrated into patient support apparatus 20, siderail nodes integrated into siderails 36 that control the occupant and caregiver user interfaces built into the siderails 36, a pendant node that controls the interaction of patient support apparatus 20 and a removable pendant that is attachable to, and detachable from, patient support apparatus 20, a headwall node that communicates with a headwall built into a room of a healthcare facility, a locator node that communicates with short-range beacons positioned at known locations in order to allow the location of patient support apparatus 20 to be determined, a propulsion node for controlling motors used to propel patient support apparatus 20 across the floor, and a propulsion interface node having sensors for determining how the user wishes to control the propulsion system. Still other modifications to control system 52 are possible.

In the embodiment shown in FIG. 2, nodes 54 include a connectivity node 54a, a graphics engine node 54b, and a user interface node 54c. Connectivity node 54a and graphics engine node 54b each include a controller 58a and 58b, respectively. Such controllers are implemented, in at least one embodiment, as conventional microcontrollers. In the illustrated example, the controllers are implemented as any one of the i.MX family of system-on-chip (SoC) processors which are marketed by Freescale Semiconductor of Austin, Tex. Other types of commercially available microcontrollers may also be used. Still further, the controllers may take on still other forms, such as any combination of any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by the controllers in carrying out the functions described herein, as well as the data necessary for carrying out these functions, are stored in one or more accessible memories (not shown).

Connectivity node 54a controls communication between patient support apparatus 20 and one or more devices that are located off-board patient support apparatus 20, including one or more off-board devices. Connectivity node 54a thus acts as a gateway between the on-board control system 52 and various external devices. As shown in FIG. 2, connectivity node 54a includes a first WiFi module 62a and a second WiFi module 62b. Each WiFi module 62 includes a WiFi transceiver (e.g. IEEE 802.11a, b, g, n, ac, ad, ah, aj, ax, and/or ay) for communicating with one or more off-board devices. In the illustrated embodiment, first WiFi module 62a is set to run in a client mode, thereby allowing patient support apparatus 20 to communicate with a wireless access point 64 of a local area network 66. Second WiFi module 62b is set to run in an access point (AP) mode, thereby allowing one or more wireless devices 68a to communicate directly with patient support apparatus 20 using WiFi. Second WiFi module 62b is in communication with first WiFi module 62a, thereby allowing wireless devices 68a to communicate with LAN 66 by transmitting messages to WiFi module 62b, which forwards the messages to WiFi module 62a, which in turn forwards the messages to access point 64 and to LAN 66. Messages may also be sent to wireless devices 68a from LAN 66 by following the reverse path.

Local area network 66 is a conventional computer network having a plurality of computers and/or servers coupled thereto. One such server is a patient support apparatus server 70. The patient support apparatus server 70 receives data from one or more patient support apparatuses 20 positioned within a healthcare facility. Patient support apparatus server 70 is configured to gather data received from the patient support apparatuses 20 located within that particular healthcare facility and share the data with one or more other servers or applications that are in communication with local area network 66.

Depending upon the particular servers installed at a particular healthcare facility, patient support apparatus server 70 may therefore communicate with a conventional Admission, Discharge, and Tracking (ADT) server operating on LAN 66 and retrieve information identifying the patient assigned to a particular patient support apparatus 20, and/or forward information regarding the current location of patient support apparatus 20 to the ADT server. Patient support apparatus server 70 may also be in communication with a conventional Electronic Medical Records (EMR) server operating on LAN 66 and both retrieve and write data to the EMR server. As one example, the retrieved data may include data that is displayed by control system 52 on user interface 50 and the written data may include one or more weight readings taken by a scale incorporated into patient support apparatus 20. Other data may also be exchanged with the EMR server.

Patient support apparatus server 70 may also communicate with one or more conventional work flow servers and/or charting servers that assign, monitor, and/or schedule patient-related tasks to particular caregivers. In some embodiments, patient support apparatus server 70 also communicates with a conventional communication server that forwards communications to particular individuals within a healthcare facility, such as via one or more portable devices (smart phones, pagers, beepers, laptops, etc.). Patient support apparatus server 70 is configured in some of these embodiments to forward alerts and/or alarms associated with a particular patient support apparatus 20 to the caregiver associated with the patient of that particular patient support apparatus 20.

LAN 66 includes at least one network appliance that is adapted to communicate with the Internet 72. The network appliance may be a conventional router and/or gateway, although other types of network appliances can be used. The network appliance allows the servers of LAN 66 to communicate with any computers that are Internet-accessible and vice versa.

In the embodiment shown in FIG. 2, a remote enterprise server 74 is coupled to the Internet and configured to allow communications with local server 70. Remote server 74 is associated with the manufacturer, seller, and/or distributor of patient support apparatuses 20. Remotes server 74, in some embodiments, gathers information regarding the use of one or more patient support apparatuses that are present in one or more healthcare facilities. Such information may include diagnostic information, usage information, and/or servicing information (including requests for servicing), as well as other information regarding patient support apparatuses 20 that is useful to the enterprise associated with patient support apparatuses 20. Further, as will be explained in greater detail below, remote server 74 provides access to software updates for patient support apparatuses 20.

Connectivity node 54a further includes a Bluetooth module 76 configured to communicate with a wireless device 68b using the Bluetooth standards (e.g. IEEE 802.15.1). In some embodiments, Bluetooth module 76 allows patient support apparatus 20 to wirelessly communicate with a headwall, location beacon, and/or nurse call system. Examples of using Bluetooth communication for such purposes are disclosed in greater detail in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication and other uses for Bluetooth module 76 may also or alternatively be implemented.

Connectivity node 54a also includes a pair of ports 78a and 78b that are adapted to receive one or more wired connectors. The wired connectors couple ports 78a and 78b of patient support apparatus 20 to one or more external devices 60a and 60b. Connectivity node 54a is thereby able to communicate with one or more external devices 60a and/or 60b via ports 78a and 78b. Ports 78a and 78b in the example shown in FIG. 2 are both power and data ports. That is, ports 78a and 78b both are capable of supplying electrical power to devices 60a and 60b, as well as sending data to and/or receiving data from devices 60a and 60b. Depending upon the particular external device 60 that is plugged into a particular port 78, the ports 78 will supply electrical power to the device 60 if needed. If the external device 60 has its own source of electrical power, and that source of electrical power is not a rechargeable source configured to be recharged via a port 78, then the port 78 will serve as a data communication link only. In some modified embodiments, however, it will be understood that one or more of the ports 78 may transfer data only, power only, and/or any combination thereof. Still further, in some modified embodiments, more than, or fewer than, two ports 78 may be provided on patient support apparatus 20.

External devices 60 may vary. In at least one embodiment, patient support apparatus 20 is configured to communicate via ports 78a and 78b with one or more of the following external devices 60: an incontinence detector placed on patient support apparatus 20 and adapted to detect incontinence in a patient support on patient support apparatus 20; a Deep Vein Thrombosis (DVT) pump adapted to apply varying pressure to one or more parts of the patient's body in order to treat, mitigate, and/or prevent DVT; a vital sign sensor adapted to detect one or more vital signs of a patient while the patient is positioned on patient support apparatus 20; a patient mobility sensor (or suite of sensors) adapted to detect movement of the patient while on and/or off patient support apparatus 20; a temperature management device adapted to cool, warm, and/or maintain the patient's body temperature; an electrical muscle stimulator adapted to electrically stimulate muscles of the patient; a patient communication device (e.g. pendant, auxiliary control panel, telephone handset, etc.) adapted to allow the patient to communicate with personnel who are positioned outside of the patient's room; a sleep detector adapted to detect one or more characteristics of the patient in order to determine if the patient is sleeping or not; a microphone adapted to detect ambient noise levels within the room; one or more cameras (visible light and/or infrared) adapted to capture images of the patient and/or the room in which the patient support apparatus 20 is located; a Voice over IP (VoIP) handset or other device adapted to allow the patient to communicate with others using VoIP technology; a pressure mapping sensor adapted to detect and map interface pressures between the patient and the surface (e.g. mattress) on which the patient is sitting or lying when positioned on top of patient support apparatus 20; one or more light sensors adapted to detect ambient light levels; a defibrillator; an infusion pump; a patient risk assessment device (e.g. for developing bed sores); a volatile organic compound (VOC) sensor adapted to detect VOC concentration levels within the vicinity of patient support apparatus 20; an electrocardiograph (ECG) sensor; a blood oxygenation and/or pulse wave velocity sensor; and a vibration therapy device for applying vibration therapy to the patient.

When one or more of the external devices 60 are implemented as thermal therapy devices, such thermal therapy devices 60 may be constructed in accordance with the thermal control units disclosed in any of the following commonly assigned U.S. patent applications: Ser. No. 14/282,383 filed May 20, 2014, by inventors Christopher Hopper et al. and entitled THERMAL CONTROL SYSTEM; Ser. No. 62/311,054 filed Mar. 21, 2016, by inventor Gregory S. Taylor and entitled MOBILE THERMAL SYSTEM; Ser. No. 62/451,121, filed Jan. 27, 2017, by inventors Martin Stryker et al. and entitled THERMAL CONTROL SYSTEM WITH FLUID CARTRIDGES; Ser. No. 62/373,658 filed Aug. 11, 2016, by inventors James Galer et al. and entitled THERMAL THERAPY DEVICES; Ser. No. 62/373,564 filed Aug. 11, 2016, by inventor James Galer and entitled THERMAL SYSTEM; and 62/361,124 filed Jul. 12, 2016, by inventor Gregory Taylor and entitled THERMAL CONTROL SYSTEM; the complete disclosures of all of which are incorporated herein by reference.

When an external device 60 is implemented in accordance with any of the thermal control units disclosed in the aforementioned patent references, the thermal control unit includes a port for connecting a cable between the thermal control unit and one of ports 78 of patient support apparatus 20. As will be explained in greater detail below, the connection of the thermal therapy device 60 to one of ports 78 allows any one or more of the following functions to be performed: displaying information from the thermal therapy device 60 on display 32 of patient support apparatus 20; controlling one or more aspects of the thermal therapy device 60 using the patient support apparatus 20's user interface 50; and supplying electrical power to thermal therapy device 60. Still other types of thermal therapy devices besides the ones disclosed in the aforementioned patent references may also or alternatively be coupled to patient support apparatus 20 via ports 78.

When one or more of the external devices 60 are implemented as an interface pressure sensing device, such interface pressure sensing devices 60 may be constructed in accordance with the interface pressure sensing devices disclosed in any of the following commonly assigned U.S. patent applications: Ser. No. 14/003,157 filed Mar. 2, 2012, by inventors Joshua Mix et al. and entitled SENSING SYSTEM FOR PATIENT SUPPORTS; Ser. No. 13/644,961 filed Oct. 4, 2012, by inventor Geoffrey Taylor and entitled PRESSURE SENSING MAT; and Ser. No. 13/802,876 filed Mar. 14, 2013, by inventor Geoffrey Taylor and entitled FORCE DETECTING MAT WITH MULTIPLE SENSOR TYPES; the complete disclosures of all of which are incorporated herein by reference.

When one or more of the external devices 60 are implemented as a volatile organic compound (VOC) sensor, the VOC sensor 60 may be constructed in accordance with the VOC sensors disclosed in commonly assigned U.S. patent application Ser. No. 62/398,577 filed Sep. 23, 2016, by an inventor Marko Kostic and entitled SYSTEM AND APPARATUS FOR DETERMINING THE USABILITY OF PERSON SUPPORT APPARATUSES, the complete disclosure of which is incorporated herein by reference.

When one or more of the external devices 60 are implemented as an electrocardiograph sensor (ECG), the ECG sensor 60 may be constructed in accordance with the ECG sensors disclosed in commonly assigned U.S. patent application Ser. No. 62/349,158 filed Jun. 13, 2016, by inventor Marko Kostic and entitled SYSTEMS AND METHODS FOR DETECTING CARDIAC ACTIVITY AND/OR INACTIVITY, the complete disclosure of which is incorporated herein by reference.

When one or more of the external devices 60 are implemented as a blood oxygenation and/or pulse wave sensor, such sensors may be constructed in accordance with the sensors disclosed in any of the following commonly assigned U.S. patent applications: Ser. No. 14/884,222 filed Oct. 15, 2015, by inventors Sean Hadley et al. and entitled SYSTEMS AND METHODS FOR DETECTING PULSE WAVE VELOCITY; Ser. No. 15/200,818 filed Jul. 1, 2016, by inventors Marko Kostic et al. and entitled SYSTEMS AND METHODS FOR STROKE DETECTION; and Ser. No. 15/185,347, filed Jun. 17, 2016, by inventor Marko Kostic et al. and entitled TISSUE MONITORING APPARATUS AND METHOD; the complete disclosures of all of which are incorporated herein by reference.

When one or more of the external devices 60 are implemented as a thermal and/or visible light cameras (and/or devices for processing the outputs from the cameras), such devices 60 may be constructed in accordance with the cameras and processing devices disclosed in any of the following commonly assigned U.S. patent applications: Ser. No. 14/692,871 filed Apr. 22, 2015, by inventors Marko Kostic et al. and entitled PERSON SUPPORT APPARATUS WITH POSITION MONITORING; Ser. No. 13/242,022 filed Sep. 23, 2011, by inventors Richard Derenne et al. and entitled VIDEO MONITORING SYSTEM; and Ser. No. 14/578,630 filed Dec. 22, 2014, by inventors Richard Derenne et al. and entitled VIDEO MONITORING SYSTEM; the complete disclosures of all of which are incorporated herein by reference.

When one or more of the external devices 60 are implemented as a chair, such chairs may be constructed in accordance with any of the chairs disclosed in any of the following commonly assigned U.S. patent applications: Ser. No. 14/212,417 filed Mar. 14, 2014, by inventors Christopher Hough et al. and entitled MEDICAL SUPPORT APPARATUS; Ser. No. 14/984,403 filed Dec. 30, 2015, by inventors Anish Paul et al. and entitled PERSON SUPPORT APPARATUS WITH PIVOTING BACKREST; and Ser. No. 14/801,167 filed Jul. 16, 2015, by inventors Anish Paul et al. and entitled MEDICAL SUPPORT APPARATUS; the complete disclosures of all of which are incorporated herein by reference.

It will be understood that other types of devices besides the specific ones mentioned and disclosed in the aforementioned patent references may also or alternatively be used and coupled to patient support apparatus 20 via ports 78. More specifically, other types of interface pressure sensing devices, VOC sensors, ECG sensors, blood oxygenation and/or pulse wave velocity sensors, image capturing and/or processing devices, and/or chairs—besides the specific ones disclosed in the aforementioned patent references—may also or alternatively be used, and coupled to ports 78 of, patient support apparatus 20.

Regardless of the specific function performed by an external device 60, the connection of the device 60 to one of ports 78 allows any one or more of the following functions to be performed: displaying information from the external device 60 on display 32 of patient support apparatus 20; controlling one or more aspects of the external device 60 using the patient support apparatus 20's user interface 50; and supplying electrical power to the external device 60. Ports 78 thereby allow certain external devices 60 that do not include their own integrated display to be coupled to patient support apparatus 20 and use the screen space (i.e. display 32) of patient support apparatus 20 to display information sensed or generated by the external device 60. Further, for those external devices 60 that do include their own screen or display, ports 78 allow information from both the external devices 60 and the patient support apparatus 20 to be consolidated onto a single display 32, thereby providing a unified display and/or control interface for multiple devices (including patient support apparatus 20). Still further, for those external devices 60 that do not include their own power source, ports 78 allow electrical power to be supplied to the devices 60 at a location closer to the patient without creating tripping hazards that might otherwise exist if the external device(s) 60 were plugged into an electrical wall outlet.

Ports 78 are configured in the illustrated embodiment to be non-standard ports. That is, the shape, size, arrangement and number of conductors within ports 78 does not conform to any well-known standards and is not adapted to be connected to any common consumer electronic cables. This non-standard configuration of ports 78 helps ensure that the chances of an external device being plugged into the port by a person not authorized by or affiliated with the healthcare facility is reduced. Further, this helps ensure that the patient and/or visitors do not attempt to recharge or use their consumer electronic devices with any of the ports 78. This also helps prevent ports 78 from being used by someone unfamiliar with the function and/or use of a port 78, or from being connected to a device not intended for interaction with patient support apparatus 20. In some embodiments, ports 78a and 78b are adapted to be used only with cables or other connectors sold by authorized representatives of the manufacturer of patient support apparatus 20, thereby further hampering the ability of a non-authorized individual to plug a cable or connector into either or both of ports 78a and 78b.

Although ports 78 are configured to be non-standard ports in the primary embodiments discussed herein, it will be understood that in some modified embodiments, one or more ports 78 may be standard ports, such as, but not limited to, a USB port (micro, mini, type A receptacle, type B receptacle, etc.) an Ethernet cable connector (e.g. an 8P8C jack or plug, a 6P6C jack or plug, a 4P4C jack or plug, etc.); a High-Definition Multimedia Interface (HDMI) plug or receptacle (types A-E); and a DB-25 or DE-9 connector used with RS-232 communications.

Figure 4:
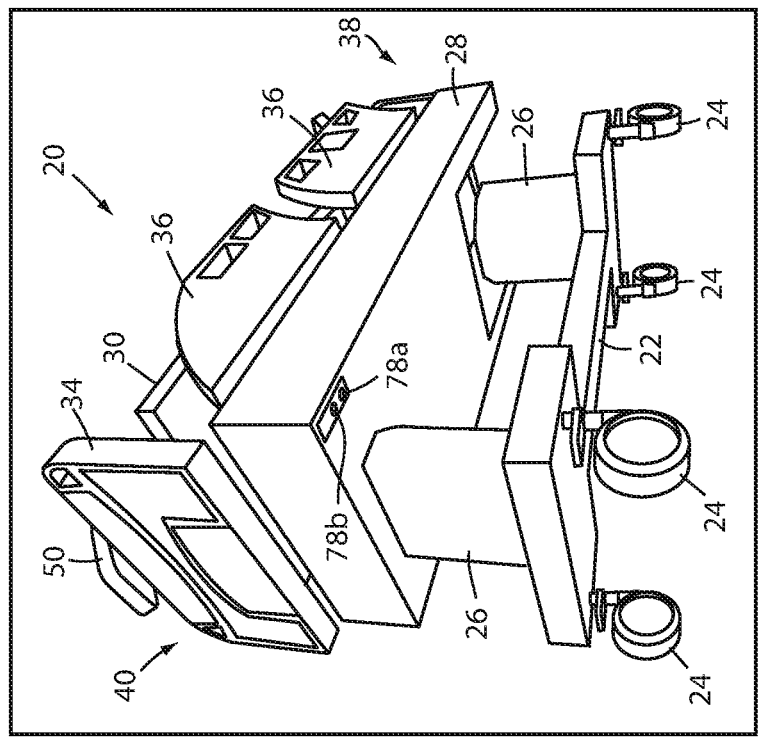
FIG. 4 is a perspective view of the patient support apparatus showing an alternative location for the plurality of external device ports.
Figure 3:
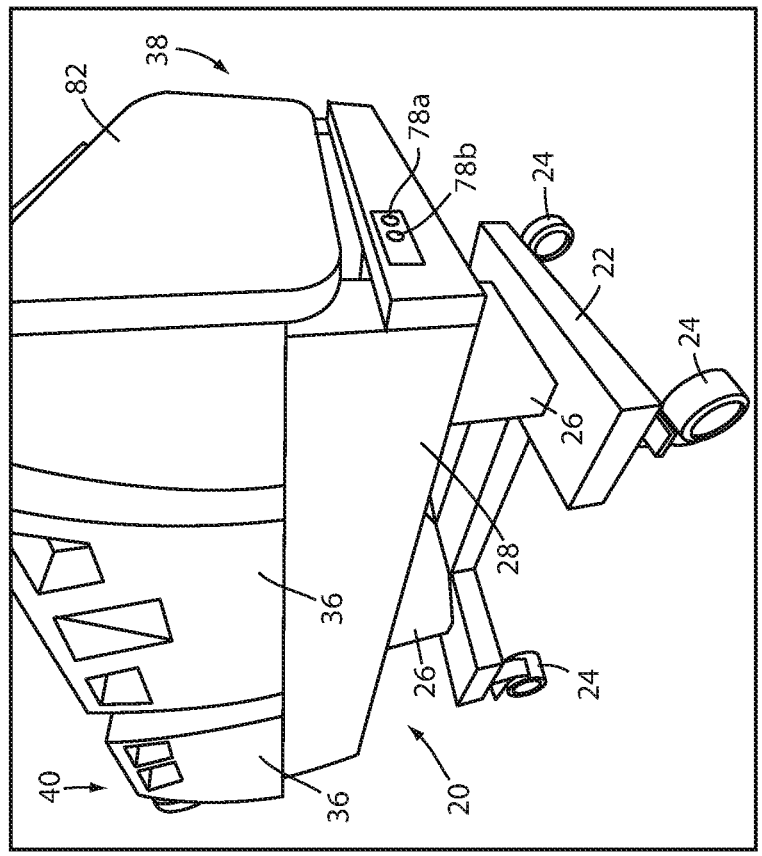
FIG. 3 is a perspective view of the patient support apparatus showing an illustrative location for a plurality of external device ports.

FIGS. 3 and 4 illustrate two different potential locations of ports 78 on patient support apparatus 20. In FIG. 3, ports 78 are located at head end 38 of patient support apparatus 20 generally underneath a headboard 82. Ports 78 in FIG. 3 are attached to the litter frame 28 and therefore remain with patient support apparatus even if headboard 82 is removed from patient support apparatus 20. Ports 78 are attached underneath the litter frame 28 generally toward foot end 40 in the patient support apparatus 20 of FIG. 4. It will be understood that still other locations for ports 78 beyond the two locations shown in FIGS. 3 and 4 are possible. Further, different number of ports 78 may be included, and in some embodiments, ports 78 are positioned at different locations on the patient support apparatus 20.

Controller 58a (FIG. 2) of patient support apparatus 20 communicates with both ports 78a and 78b via a communication medium 56a, which may be any suitable communication medium, such as, but not limited to, a Controller Area Network bus, an Ethernet link, a FireWire link, a Serial Peripheral Interface (SPI), an RS-232 or RS-485 link, an I-squared-C link, or still another type of communication medium. Communication medium 56a may be the same as, or different from, other communication media 56 used on patient support apparatus 20.

In at least one embodiment, each port 78 includes a designated conductor and a designated ground pin that are together used to implement the standard 1-wire device communication bus system designed by Dallas Semiconductor Corp. In such an embodiment, each external device 60 includes an initial communication structure 80 (FIG. 2) that initially communicates with a port 78 of patient support apparatus 20 via the 1-wire conductor. In at least one embodiment, the initial communication structure 80 is a 1-wire Electronically Erasable Programmable Read Only Memory (EEPROM). When implemented as such an EEPROM, the communication structure may be specifically implemented as a DS24B33 1-wire 4 Kilobit EEPROM from Maxim Integrated Products, Inc. of San Jose, Calif. Other types of 1-Wire EEPROMs can, of course be used.

When implemented as a DS24B33 1-wire 4 Kilobit EEPROM from Maxim Integrated Products, each initial communication structure 80 includes a unique, factory programmed, 64-bit registration number that uniquely identifies the particular external device 60 that is coupled to a port 78. Controller 58a reads this unique registration number when the external device 60 is initially plugged into port 78 using the 1-Wire communication protocol. After reading this unique identifier, controller 58a determines if the registration number corresponds to an approved device. Controller 58a determines this by comparing the unique registration number to a list of authorized registration numbers maintained in a memory on-board patient support apparatus 20. This list may alternatively or additionally be stored on local server 70 and/or remote server 74. In such cases, controller 58a either retrieves the list from server 70 or 74, or sends the unique registration number to server 70 and 74 and requests that those servers determine if the unique registration number corresponds to an authorized device. The results of the determination are then sent back to patient support apparatus 20. If the device is not on the list of authorized devices, then controller 58a terminates communication with external device 60 and does not provide any electrical power to the device.

The list of authorized registration numbers originates from the manufacturer of the patient support apparatus 20, in some embodiments. The manufacturer works with one or more third party manufacturers of external devices 60 who wish to allow their devices 60 to utilize the user interface of patient support apparatus 20. The manufacturer of patient support apparatus 20 provides such authorized third parties with a set of unique registration numbers which are then incorporated into the authorized external devices 60. This set is combined with other sets (if any) of other authorized third party manufacturers to form the aforementioned list, which patient support apparatus 20 uses to determine if an authorized devices has been plugged into a port 78.

In addition to the unique registration identifier, initial communication structure 80 includes a device type identifier and device property stored therein. When initial communication structure 80 is implemented as a 1-wire EEPROM, the device type identifier and device property data are stored at locations within the EEPROM that are either predetermined and known to controller 58a, or are accessible to controller 58a by sending a request for such information to external device 60 using the 1-Wire connection. The device type identifier identifies the type of device that external device 60 is. In other words, the device type identifier tells controller 58a whether external device 60 is an incontinence detector; a (DVT) pump; a vital sign sensor; a patient mobility sensor (or suite of sensors); a patient temperature management device; an electrical muscle stimulator; a patient communication device; a sleep detector; a microphone; an imaging device; a Voice over IP (VoIP) handset; a pressure mapping sensor; a light sensor; a defibrillator; an infusion pump; a VOC sensor; an ECG sensor; a blood oxygenation and/or pulse wave velocity sensor; a vibration therapy device, or another type of device.

The device properties data tells controller 58a various properties of the device, such as, but not limited to, the types of data generated by the external device 60; whether the external device 60 only displays data on one or more screens of user interface 50 or also allows the external device 60 to be controlled by one or more controls of user interface 50; what pins of port 78 external device 60 will use to communicate with patient support apparatus 20 (including pins within port 78 that are separate from and additional to the ground pin and single conductor pin used to communicate using the 1-wire protocol); what communication protocol external device 60 uses for communication; and other information used by controller 58a for communicating with external device 60.

After receiving the device type identifier from the initial communication structure 80, controller 58a uses the device type identifier to determine whether patient support apparatus 20 possesses a software package that enables control system 52 of patient support apparatus 20 to perform one or more of the following functions: display information from the external device 60 on one or more displays 32 of patient support apparatus; control one or more aspects of the external device using one or more controls of the patient support apparatus user interface 50; and provide electrical power to the external device 60. If patient support apparatus 20 does not possess this software, or does not possess the latest version of this software, controller 58a sends a message to local server 70 via access point 64 requesting this software, or the latest version of this software. Local server 70 forwards the requested software to patient support apparatus 20, which then uses the software to enable the external device 60 to display data on, be controlled by, and/or receive power from patient support apparatus 20. A caregiver or other user of the external device 60 can then use a single consolidated user interface (user interface 50 of patient support apparatus 20) for controlling and viewing data from both external device 60 and patient support apparatus 20.

Graphics node 54b (FIG. 2) controls the graphics that are displayed on one or more displays of patient support apparatus 20, such as display 32. At least one such display 32 is incorporated into footboard 34 and may be positioned adjacent, or integrated into, user interface 50. One or more additional displays 32a may also be included, such as one or more displays mounted to siderails 36. In other embodiments, the display 32 of footboard 34 is moved to a different location on patient support apparatus 20. In any of the embodiments disclosed herein, the display 32 may be configured to function only as a display, or it may be configured as a touchscreen display that is sensitive to user touch.

Graphics node 54b includes memory for storing the graphics that are displayed on the one or more displays 32, as well as programming instructions for carrying out the display of those graphics. In some embodiments, graphics node 54b delivers graphics to the display that are organized in a scalable vector graphics (SVG) format. In other embodiments, graphics node 54b delivers graphics using another format.

In the embodiment shown in FIG. 2, graphics node 54b communicates with connectivity node 54a via an Ethernet connection 56b. Such communication is carried out via Ethernet transceivers 84. In some modified embodiments of patient support apparatus 20, additional nodes besides connectivity node 54a and graphics node 54b communicate via Ethernet, and patient support apparatus 20 includes an Ethernet switch for routing Ethernet frames between the various nodes. One suitable design for such Ethernet-connected nodes is disclosed in commonly assigned U.S. patent application Ser. No. 14/622,221 filed Feb. 13, 2015, by inventors Krishna Bhimavarapu et al. and entitled COMMUNICATION METHODS FOR PATIENT HANDLING DEVICES, the complete disclosure of which is incorporated herein by reference. Other types of inter-node communication, as well as other arrangements of nodes may also be used.

Graphics node 54b is communicatively coupled to user interface node 54c (FIG. 2) by way of two communication media 56c and 56d. In the illustrated embodiment, communication medium 56c is an I-Squared-C or RS-485 connection between a pair of transceivers 88 adapted to support I-Squared-C and/or RS-485 communication. Communication medium 56d is a Low Voltage Different Signal (LVDS) connection (i.e. a TIA/EIA-644 connection) between a pair of LVDS transceivers 90. Communication medium 56c handles communications between graphics node 54b and user interface 50, including display 32. Communication medium 56d handles communications between graphics node 54b and display 32a which, as noted, is positioned at a location spaced apart from display 32 of user interface 50 (e.g. display 32 may be located on footboard 34 with display 32a located on one of siderails 36).

User interface node 54c (FIG. 2) oversees and controls user interface 50 of footboard 34. User interface 50, in at least some embodiments, includes a plurality of buttons for activating and deactivating motors used to move various components of patient support apparatus 20. Such buttons, or other controls, are coupled to a button interface 86 that communicates with controller 58b of graphics node 54b via communication medium 56c and transceivers 88. In addition to controlling movement of patient support apparatus 20, user interface 50 also allows a user to take weight measurements of a person supported on patient support apparatus 20, configure alert settings, and control other aspects of patient support apparatus 20. Further, as mentioned above and described in more detail below, user interface node 54c displays data from one or more external devices on display 32 and/or display 32a, and allows one or more controls of patient support apparatus 20 to be used for controlling one or more aspects of one or more external devices 60. User interface node 54c carries out the user commands (for both patient support apparatus 20 and external devices 60) by sending messages to graphics node 54b and/or connectivity node 54a. User interface node 54c also displays data regarding patient support apparatus 20 and one or more external devices 60 by receiving the data to be displayed from graphics node 54. That is, user interface node 54c is responsible for carrying out the display of graphics whose content is supplied by graphics engine node 54b.

In the embodiment illustrated in FIG. 2, user interface 50 also includes an RFID reader 92. RFID reader is adapted to read badges, cards, or the like, that are worn or carried by authorized individuals within a healthcare facility and that contain RFID chips. Such badges or cards are detected by RFID reader 92 when the authorized individual is positioned within a close proximity to user interface 50. When RFID reader 92 detects the presence of an authorized individual within close proximity to user interface 50, user interface node 54c automatically performs one or more of the following: enables one or more controls of user interface 50 based upon the particular RFID badge or card detected; disables one or more controls of user interface 50 based upon the particular RFID badge or card detected; automatically displays a particular set of data on display 32 and/or display 32a based upon the particular RFID badge or card detected; and automatically records the time at which the authorized individual is detected and/or the identity of the authorized individual. When recording the identity of an authorized individual, patient support apparatus 20 may be configured to automatically record and/or chart actions taken with respect to patient support apparatus 20 and/or its associated patient as being performed by the particular individual associated with the detected RFID badge or card.

FIG. 5 illustrates an example of a communication method 94 for enabling communication between patient support apparatus 20 and authorized external devices 60. Communication method 94 begins at a step 96 where one or more external devices 60 are connected to one or more of ports 78. Ports 78 are configured to detect when a cable or other connector is physically coupled thereto. In addition to detecting the presence of a port-coupled external device 60 at step 96, controller 58a also reads the external device authentication identifier and the device type identifier (if the two identifiers are different—in some embodiments a single identifier serves both purposes of authentication and identification). As noted previously, in some embodiments, the authentication number refers to a 64-bit registration number of a 1-Wire EEPROM contained within external device 60. In other embodiments, a different device authentication identifier is used.

Once controller 58a of connectivity node 54a receives the device type identifier from external device 60 at step 96 (FIG. 5), it checks to see if it currently has a software package 106 on board patient support apparatus 20 that enables it to fully communicate with external device 60. If this software package 106 is not present, controller 58a sends a request for the software package 106 to local server 70 at a step 98. Local server 70 is loaded with the software package by a technician when the healthcare facility purchases external device 60 or patient support apparatus 20, or at other times. The software package is purchased or leased from, in at least some embodiments, the manufacturer of either patient support apparatus 20 or the external device 60, although it will be understood that other entities may be authorized to provide the software package.

Local server 70, in some embodiments, stores multiple software packages 106 used for communicating with different types of external devices 60. Each software package 106 bears an identifier that enables local server 70 to match the particular software package to a particular external device 60. Thus, for example, local server 70 may contain a first software package for communicating with a DVT pump 60, a second software package for communicating with a vital sign sensor 60, and a third software package for communicating with an incontinence detector. In some instances, local server 70 may contain multiple software packages for communicating with a single type of external device 60 wherein each package corresponds to a different brand, model, and/or sub-type.

For example, local server 70 may contain a first software package 106 for communicating with a brand X DVT pump, a second software package 106 for communicating with a Brand Y, model A DVT pump, and a third software package for communicating with a Brand Y, model B DVT pump 60. Still further, local server 70 may contain different software versions for the software packages that correspond to different updates for the various software packages. Local server 70 determines which software package (including the version number) is used for a particular external device 60 based upon the external device identifier received from external device 60 and a software identifier that identifies each piece of software stored thereon.

In some embodiments, local server 70—which may be provided to the healthcare facility by the same entity who provides patient support apparatus 20 or external device 60—is configured to automatically communicate with one or more remote servers 74 and retrieve the software package 106 required for communicating with a particular external device 60 from that remote server 74 via the Internet 72. This retrieval is carried out periodically, in some embodiments, to help ensure that local server 70 includes the latest versions of software used by patient support apparatus 20 for communicating with the external devices 60. In other embodiments, the retrieval of the software package is carried out in response to a request from a patient support apparatus 20 for the particular software package.

After the software package is delivered by local server 70 to patient support apparatus 20, controller 58a of patient support apparatus 20 unpackages the software package 106 at step 100 (FIG. 5). During unpackaging step 100, controller 58a also verifies the integrity of the software package 106 by checking one or more identifiers associated with the software package and the information received from initial communication structure 80. After the software package has been verified, the software is installed for use on patient support apparatus 20.

Controllers 58a and 58b use the software package 106 to present one or more modified user interface screens on display 32 (or display 32a), in at least some embodiments. The modified user interface screen is displayed at step 102 of method 94. The modified user interface screen, as will be discussed in more detail below, presents information about both patient support apparatus 20 and the connected external device to the user. Further, in some embodiments where the display 32 or 32a is a touchscreen, the modified user interface screen may include one or more control elements (e.g. button icons, sliders, etc.) for the connected external device 60, in addition to the regular control elements displayed thereon for controlling aspects of patient support apparatus 20. The downloaded software package therefore allows patient support apparatus 20 to provide a display for displaying data from the external device and, for at least some external devices, provide a user interface for the external device 60.

Step 104, which automatically updates the software package 106 in order to help ensure that patient support apparatus 20 is executing the most up-to-date version of the software package, is carried out in one of two different manners (FIG. 5). In a first manner, step 104 automatically updates the software package by having patient support apparatus 20 periodically communicate with local server 70 to see if a more up to date software package is available. If it is, local server 70 sends the more up to date software package to patient support apparatus 20, which then commences use of the more up to date software package. In a second manner, step 104 is carried out by local server 70 automatically sending the most up to date software package to patient support apparatus 20 whenever local server 70 receives a more up to date software package (such as from a technician installing the more up to date software on local server 70, or from downloading it from a remote server, such as remote server 74.

Figure 6:
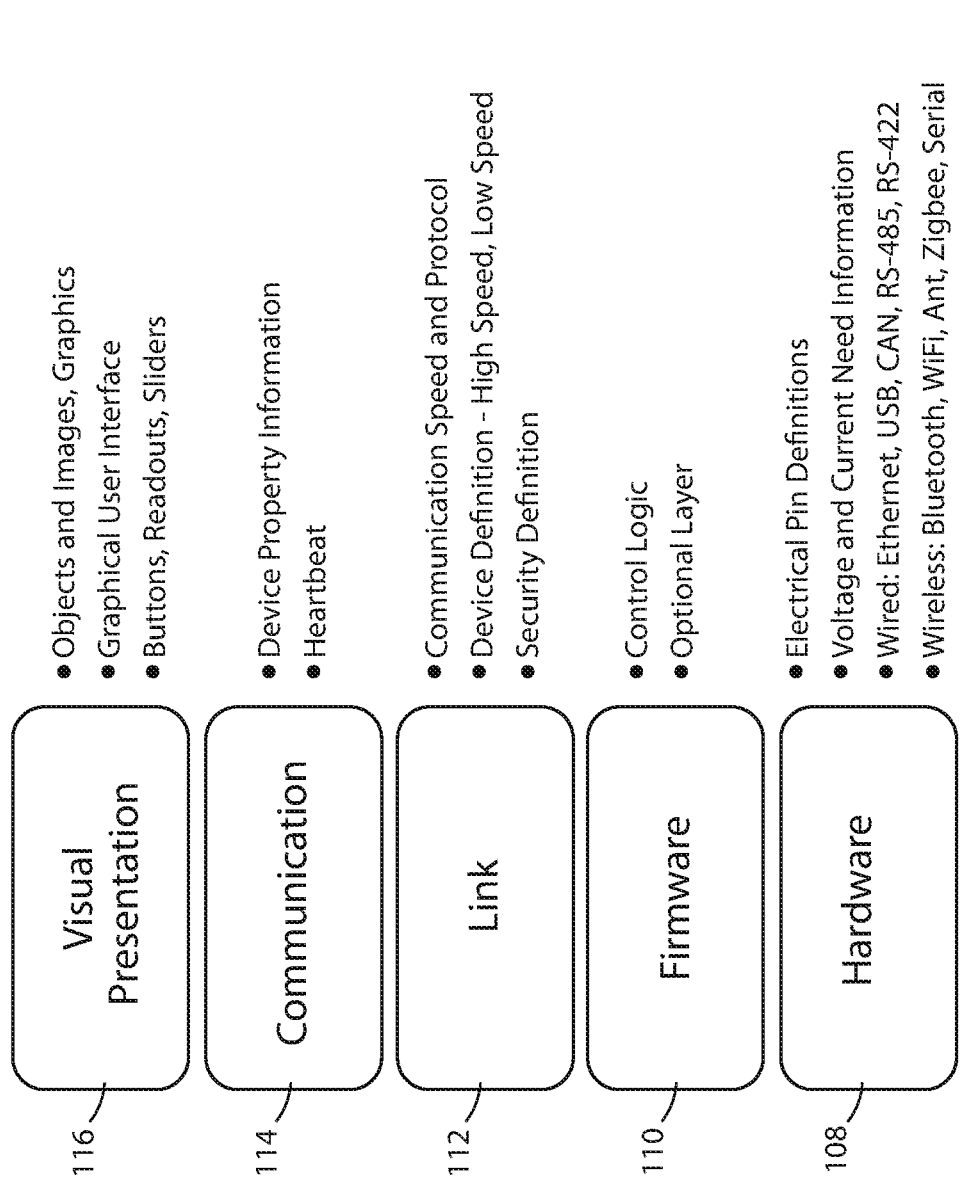
FIG. 6 is a block diagram showing various properties of the software installed during the method of FIG. 5.

FIG. 6 illustrates in more detail the contents of a representative software package 106 that may be downloaded to patient support apparatus 20 as part of communication method 94. In this representative example, software package 106 includes a hardware portion 108 that defines and informs controller 58a of various hardware aspects of the communication circuitry of external device 60. These hardware aspects include defining the electrical characteristics of each of the pins used by external device 60 when communicating with patient support apparatus 20, and well as the voltages used with those pins, the electrical current needs, if any, of external device, and the communication protocol used by external device. In some embodiments, the communication protocol is an Ethernet, USB, Controller Area Network (CAN), RS-485, or RS-422 protocol. Other protocols, however, may be used. Still further, as will be discussed in greater detail below, in some embodiments a wireless protocol is used and ports 78 are replaced by wireless ports adapted to wirelessly communicate with one or more external devices 60. Such wireless communication may take place via Bluetooth, WiFi, Ant, ZigBee, or a wireless serial protocol.

In addition to hardware portion 108, software package 106 also includes a firmware portion 110 that defines the control logic that can be used by controller 58a to control external device 60 (if external device 60 is controllable by patient support apparatus 20), as well as any optional control features that may be associated with a particular external device. The control logic tells controller 58a what signals to send to external device 60 in response to inputs received from user interface 50 of patient support apparatus 20. Thus, for example, if a user activates a control on user interface 50 that is designed to, say, set an alert condition for an external device 60, firmware portion 110 includes instructions for converting the inputs received at user interface 50 (and communicated to controller 58a through graphics node 54b) into commands for transmitting to external device 60.

Software package 106 also includes a link portion 112 (FIG. 6) that defines the speed of communication between patient support apparatus 20 and external device, as well as any special protocols used for carrying out that communication. Link portion 112 also defines what kind of security, if any, is used with the communication between patient support apparatus 20 and external device 60. For some external devices 60, one or more separate communication protocols are used for communication with patient support apparatus 20 in addition to the 1-wire protocol discussed above. In such embodiments, controller 58a first uses the 1-wire communication protocol to communicate with initial communication structure 80 of the external device 60 and to receive the device identifier, authentication identifier, and device properties. After software package 106 is received, a different communication protocol may be used for communication between patient support apparatus 20 and external device 60. The lower levels of the communication protocol are specified in the hardware portion 108 of software package 106, as mentioned above, and the upper layers of the communication protocol are defined in the link portion 112.

As one example, port 78 may include a CAN transceiver, RS-485 transceiver, an Ethernet transceiver, or other type of transceiver that is different from the transceiver used for communicating with initial communication structure 80. If the external device communicates using Ethernet, hardware portion 108 provides the Ethernet specifications while link portion 112 may provide one or more higher level communication protocols (e.g. TCP/IP, FTP, etc.). Alternatively, if the external device 60 communicates using CAN or RS-485, hardware portion 108 provides the software for implementing the physical layers and/or data link layers (of the OSI model) of the CAN or RS-485 protocols, while link portion 112 provides the software for implementing one or more higher level layers (e.g. network layer, transport layer, application layer) that are used with the CAN or RS-485 protocols. Indeed, in some embodiments, port 78 is adapted to communicate using multiple different types of protocols, thereby enabling different external devices 60 that use different communication protocols to be coupled to patient support apparatus 20. One suitable manner of enabling such multi-protocol communication is disclosed in commonly assigned U.S. patent application Ser. No. 62/464,565, which was previously incorporated herein by reference. Such multiple protocols includes, but are not limited to, CAN, RS-485, Ethernet, Local Interconnect Network (LIN), Firewire, RS-232, Universal Serial Bus (USB), RS-422, LONWorks, and/or a Serial Peripheral Interface (SPI).

A communication portion 114 of software package 106 defines additional properties about external device 60, including, but not limited to, a communication heartbeat that is used between patient support apparatus 20 and external device 60 so as to maintain knowledge of the continued communicative coupling and functionality of each other.

A visual presentation portion 116 of software package 106 defines the graphics, images, objects, buttons, readouts, sliders, and the like that are displayed on displays 32 and/or 32a of patient support apparatus 20 when displaying data from external device 60. This data is forwarded to controller 58b of graphics node 54b which uses it to determine the content to display on displays 32 and/or 32a. Visual presentation portion 116 also defines which one of displays 32 and/or 32a to display data and/or commands on. Such definitions may include displaying different data, graphics, formats, controls, and/or layouts on the various displays 32, 32a, etc. of patient support apparatus 20. For some software packages 106, the same data, graphics, formats, controls, and/or layouts may be used for all of the displays 32, 32a, etc. that are present on patient support apparatus 20.

Each software package 106 is created, in some embodiments, through collaboration with the manufacturer of patient support apparatus 20 and the manufacturer of one or more external devices 60 designed to communicate with patient support apparatus 20. The collaboration includes the sharing of the interface properties of the external device 60 with the manufacturer of patient support apparatus 20. The software package is thereafter created, tested, and certified by one or both of the companies. After being certified, one or both of the companies (or their authorized representatives) sell, lease or otherwise provide the software package 106 to one or more healthcare facilities. The software package 106 is delivered to a server on the healthcare facilities local area network (e.g. local server 70). The delivery may involve a person physically installing the software package on the local server 70, or it may involve installing the software remotely by sending it from remote server 74 to local server 70. Once installed on local server 70, local server 70 may retain the software package 106 until a patient support apparatus 20 in communication with local server 70 requests the software package (in response to the corresponding external device 60 being plugged into a port 78), or it may forward the software package to the patient support apparatuses 20 without waiting for such a request.

Local server 70, in some embodiments, maintains a listing of all of the software packages 106, including version numbers, that have been transmitted to each of the patient support apparatuses 20 it is in communication with. Local server 70 uses this list to automatically update those patient support apparatuses 20 that have a software package 106 on them when local server 70 receives an updated version of that particular software package 106. In some embodiments, local server 70 maintains a listing of all of the types of patient support apparatuses 20 maintained within a healthcare facility and periodically requests from one or more remote servers, such as remote server 74, updated versions of any software packages that are available for the particular types of patient support apparatuses 20 at that particular healthcare facility.

FIGS. 7-10 illustrate examples of the types of screens that may be displayed on display 32 of patient support apparatus 20 when an external device 60 that is adapted to measure a patient's vital signs is coupled to a port 78 of patient support apparatus 20. It will be understood that, although FIGS. 7-10 are described herein with respect to display 32, the screen shots of those FIGS. may alternatively or additionally be displayed on display 32a.

Figure 7:
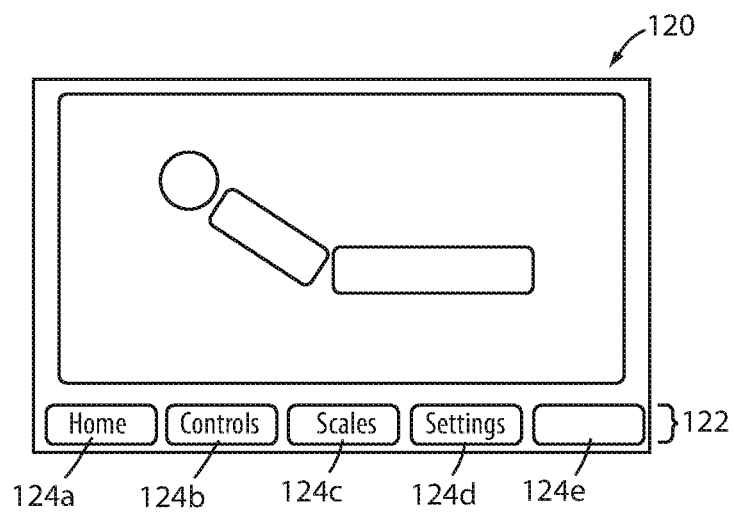
FIG. 7 is an illustrative screen shot of a user interface of the patient support apparatus showing a menu of control options for only the patient support apparatus.

FIG. 7 illustrates a screen shot 120 displayed by graphics node 54b on display 32 when no external device 60 is coupled to any of ports 78. Thus, the content of screen shot 120 is displayed using software that is pre-loaded on patient support apparatus 20, and does not utilize a software package, such as software package 106, to display this content. Screen shot 120 includes a menu bar 122 positioned generally along its bottom. Menu bar 122 includes a plurality of menu options 124a-e. Screen shot 120 is intended to be displayed on a touch screen such that a user is able to press on different areas of the screen shot to carry out different actions.

In the example of FIG. 7, if a user presses on the "home" menu option 124a, graphics node 54b displays a home screen, such as the screen shown in FIG. 7. If the user presses the "controls" menu option 124b, graphics node 54b displays a control screen in which controls for various functions of the patient support apparatus 20 are displayed and, when pressed, effectuate control of the corresponding functions of patient support apparatus 20. If the user presses the "scales" menu option 124c, graphic node 54b displays a screen having controls for controlling a built-in scale of patient support apparatus 20. If the user presses "settings" menu option 124d, graphics node 54b displays a screen showing various settings that may be adjusted by the user, such as, but not limited to, the current time and date, the language to be used, the units of measure to display, alarm setting and preferences, etc. Menu option 124e is left blank in screen shot 120 and controller 58b takes no action in response to a user pressing menu option 124e. In some embodiments, menu option 124e is eliminated from screen shot 120.

Figure 8:
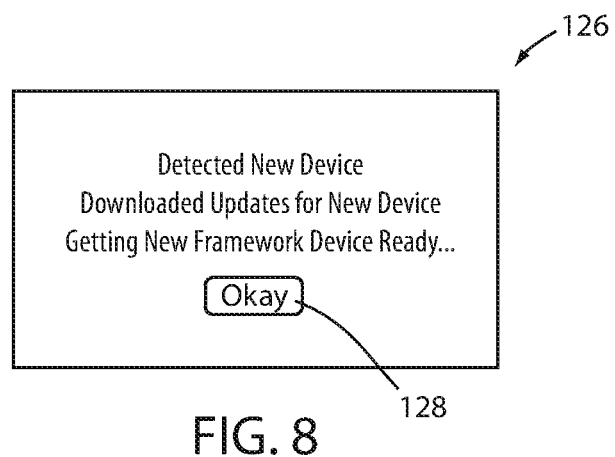
FIG. 8 is an illustrative screen shot of the user interface of FIG. 7 showing an example of an image displayed while software for use with the external device is downloaded to the patient support apparatus.

FIG. 8 illustrates an example of a screen shot 126 displayed on display 32 by controller 58*b* in response to detecting that an external device 60 has been plugged into one of ports 78. Screen shot 126 is displayed when controller 58*a* detects the presence of a coupled external device 60 and is in the process of obtaining the software package 106 (if not already present on patient support apparatus 20) corresponding to the specific external device 60 that has been detected. Screen shot 126 includes an OK option 128 that a user may press to acknowledge the presence of the new external device 60 and the retrieval of its corresponding software package 106. In some modified embodiments, screen shot 126 may include an optional "cancel" option, or the like, allowing the user to prevent the external device 60 from communicating with patient support apparatus 20.

Figure 9:
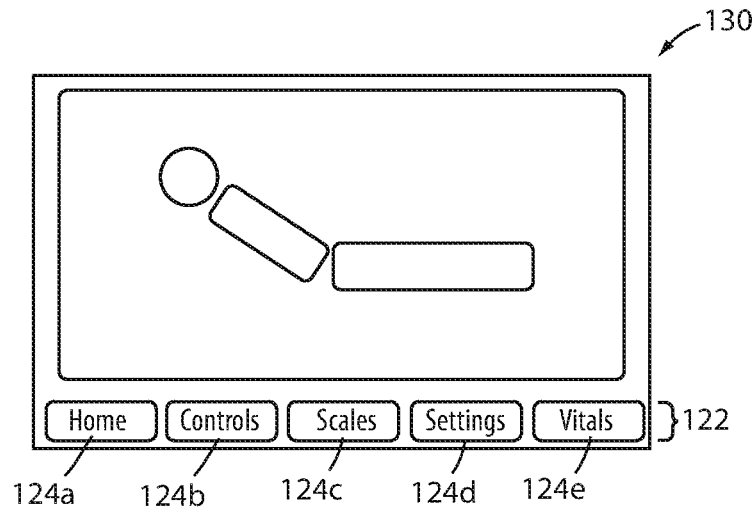
FIG. 9 is an illustrative screen shot of a user interface of the patient support apparatus showing a menu of control options for both the patient support apparatus and an external device used to measure the patient's vital signs.

FIG. 9 illustrates an example of a screen shot 130 displayed on display 32 by controller 58*b* after external device 60 has been identified. As can be seen therein, screen shot 130 differs from screen shot 120 of FIG. 7 in that menu option 124*e* of FIG. 9 has been labeled with the term "vitals." This label has been added because, in this particular example, the connected external device 60 is a vital sign sensor adapted to measure one or more vital signs of the patient. In some embodiments, screen shot 130 is displayed using only the software that pre-exists on patient support apparatus 20. That is, in some embodiments, controller 58*b* is able to display the entire contents of screen shot 130 without utilizing any software package 106. In such embodiments, the label for menu option 124*e* is determined by controller 58*b* based upon the device authentication and/or device type identifier that is communicated to patient support apparatus 20 from initial communication structure 80. In such embodiments, the software package 106 is utilized only after a user presses on, or otherwise selects, menu option 124*e*.

Figure 10:
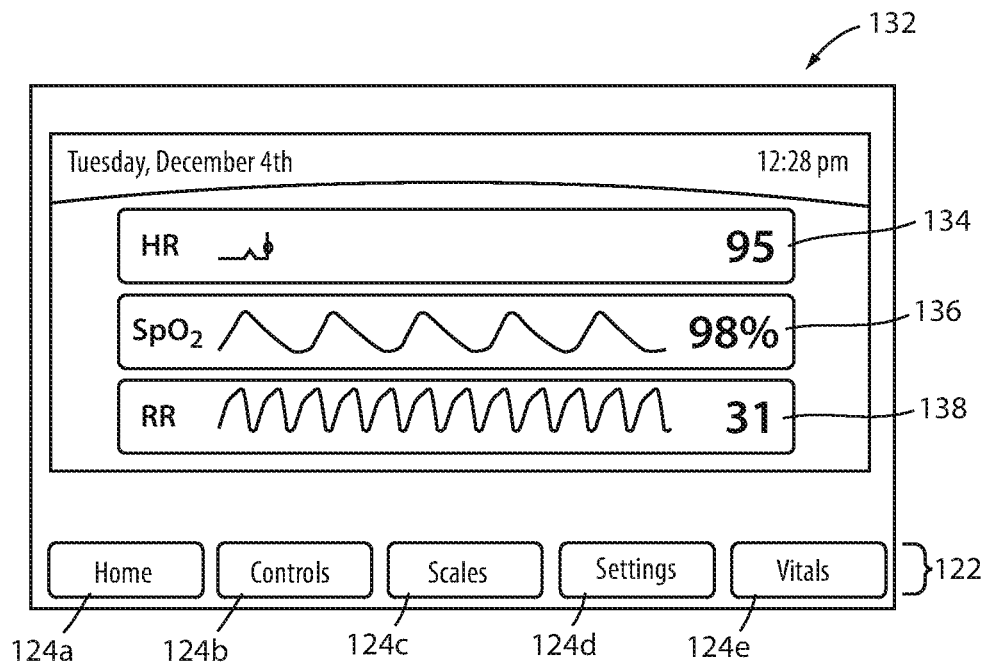
FIG. 10 is an illustrative screen shot showing an example of the type of information displayed on the user interface when the "vitals" option of FIG. 9 is selected by a user.

FIG. 10 illustrates an example of a screen shot 132 displayed on display 32 by controller 58*b* after a user has selected the "vitals" menu option 124*e* of screen shot 130 (FIG. 9). Screen shot 132 includes a heart rate section 134 that displays the patient's current heart rate and blood pressure, an oxygen saturation section 136 that displays the patient's oxygen saturation, and a respiration rate section 138 that displays the patient's current respiration rate. The measurements displayed in sections 134, 136, and 138 come from external device 60. The format, graphics, arrangement, and layout of sections 134, 136, and 138 are dictated by a software package 106 that was downloaded by patient support apparatus 20 and that corresponds to the particular vital signs external device 60 that is currently plugged into one of ports 78.

Depending upon the particular software package 106 that was downloaded for patient support apparatus 20 in the example of FIG. 10, a user of patient support apparatus 20 may be able to activate or select one or more areas of sections 134, 136, and/or 138 to view more detailed information that has been derived from vital signs external device 60, and/or to control one or more aspects of the vital signs external device 60. For example, with some software packages, if the user selects the heart rate section 134, controller 58*b* uses the corresponding downloaded software package 106 to display additional information about the patient's heart rate, such as a history of the patient's heart beat, the average, median, or other statistical information regarding the patient's heart rate, and/or any other information sensed by external device 60 that relates to the patient's heart and that isn't displayed on screen shot 132. Similar additional information may be displayed when the user selects oxygen saturation section 136 and/or respiration rate section 138.

Figure 11:
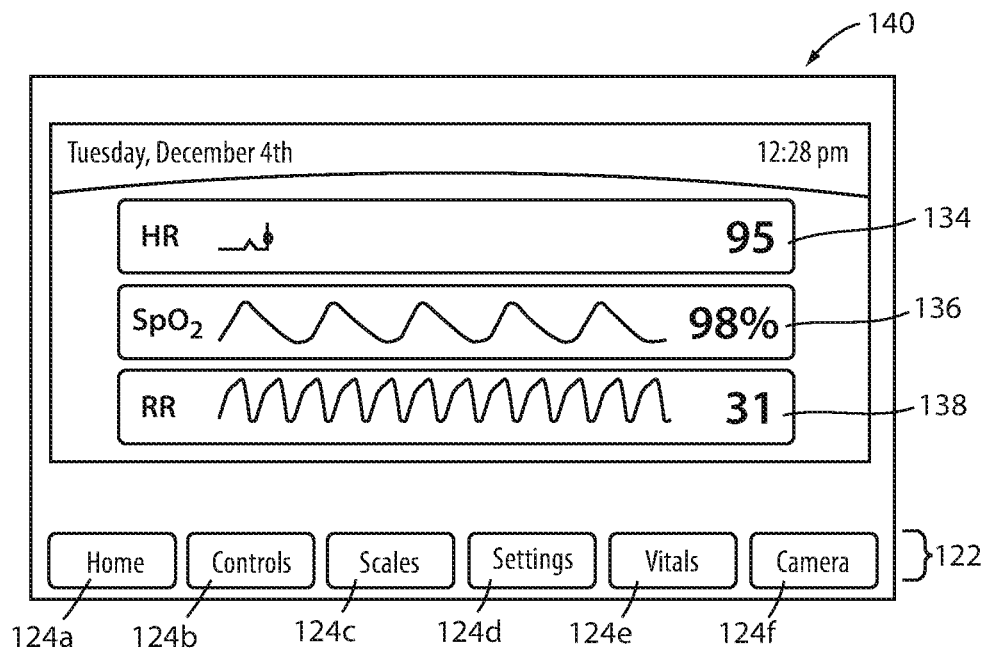
FIG. 11 is an illustrative screen shot similar to that of FIG. 10 but changed to include a control option for a second external device (a camera)

FIG. 11 illustrates an example of a screen shot 140 displayed on display 32 by controller 58*b* after a user has coupled a second external device 60 to the other of ports 78 of patient support apparatus 20. Specifically, screen shot 140 provides an illustrative example of what is displayed on display 32 when, after the vital signs external sensor of FIG. 10 has been coupled to patient support apparatus 20, a camera external device 60 is also coupled to patient support apparatus 20. Controller 58*b* alters the menu bar 122 such that it includes an additional menu option 124*f*. Menu option 124*f* corresponds to the added camera external device 60. When camera 60 is first coupled to patient support apparatus 20, controller 58*a* follows the previously described steps. That is, controller 58*a* reads the device identifier and authentication identifier from the camera 60, checks to see if patient support apparatus 20 has a software package 106 that corresponds to that particular camera 60, or type of camera 60, retrieves the software package 106 from local server 70 if it is not on-board patient support apparatus 20 already, and then uses that software package 106 in conjunction with display 32 (and/or 32*a*) in response to a user selecting menu option 124*f*.

If a user selects menu option 124*f*, controller 58*b* of graphics node 54*b* switches from displaying the heart rate, oxygenation, and respiration rate sections 134, 136, and 138 to displaying images, controls, and/or other data, from the camera 60. The images, controls, and/or other data (except menu bar 122) that is displayed on display 32 in response to menu option 124*f* being selected is determined by the software package 106 that was downloaded for camera 60. If a displayed control is activated or otherwise selected by a user, controller 58*b* detects this and forwards information regarding this detected activation to controller 58*a* of connectivity node 54*a*. Controller 58*a* uses the downloaded software package 106 for camera 60 to determine what message to send to camera 60 via its corresponding port 78 in response to that particular control being activated or otherwise selected. Thus, for example, if the user selects a "zoom" control on display 32, controller 58*a* is informed of this selection from controller 58*b*, and controller 58*a* determines from the camera software package 106 the contents of a "zoom" command to send to camera 60. The format of the command is also determined based upon information from the software package 106 for camera 60. Controller 58*a* sends the "zoom" command to camera 60, which responds by increasing the focal length of the camera 60.

In some instances, after a user activates a control on display 32 for an external device 60 and controller 58*a* sends the corresponding command to external device 60, external device 60 responds to controller 58*a* with one or messages indicating changes that should be made to the content shown on display 32. For example, if a user activates a command to change a value of a setting of an external device 60 using patient support apparatus user interface 50, controller 58*a* may receive, after sending the appropriate setting change command to external device 60, a responsive message from external device 60 instructing it to display the value of the changed setting on display 32. In response to this message, controller 58*a* tells controller 58*b* of the responsive message and controller 58*b* updates the content of the data displayed thereon to show the changed value of the setting. In this manner, controllers 58*a* and 58*b* receive real time feedback from external device 60, thereby allowing display 32 to present up to date information regarding not only the data being sensed by external device 60, but also the present state of external device 60.

Although patient support apparatus 20 has been described primarily herein as downloading the software package 106 corresponding to a particular external device 60 from local server 70, it will be understood that, in some modified embodiments, the software package 106 is stored on the external device 60 itself and downloaded via port 78. Controller 58a determines if the software package for a particular external device 60 is present on the device itself during its initial communication with initial communication structure 80, which is programmed by the manufacturer of device 60 to include information indicating whether a software package 106 is stored on external device 60 itself or not. In such embodiments, initial communication structure 80 either stores the software package 106 itself, or includes instructions for how to read the software package 106 from external device 60. Controller 58a reads this data and uses it to download the software package 106 from the external device 60 itself. Once downloaded and installed on patient support apparatus 20, controller 58b modifies user interface 50 of patient support apparatus 20 to provide for the control of, and/or the display of data from, external device 60 via user interface 50. In some of these embodiments, controller 58a is also programmed to automatically check for a more up to date version of the software package received from external device 60 by sending a request to local server 70. If a more up to date version exists, controller 58a downloads the more up to date version, rather than, or subsequent to, the software package 106 stored on the external device 60.

Figure 13:
FIG. 13 is another table of exemplary external devices and their associated properties that may be coupled to the patient support apparatus to utilize the display and/or controls of the patient support apparatus.

FIGS. 12 and 13 illustrate two tables 150a and 150b that provide two exemplary lists of the types of external devices 60 that may be coupled to patient support apparatus 20 to utilize the display and/or controls of the user interface 50 of patient support apparatus 20. The exemplary external devices 60 that may be coupled to patient support apparatus 20 are listed in the left-most column 142. The features of the external devices 60 that are displayable and/or controllable on the user interface 50 of patient support apparatus 20 are displayed in the second column 144. The units used to measure or describe the feature displayed in column 144 are shown in the third column 146. The last column indicates whether the features are only displayable on a display (32 or 32a) of user interface 50 of patient support apparatus 20, or are only controllable by user interface 50, or are both displayable and controllable via user interface 50.

For example, if the external device 60 is a chair and the chair is coupled to one of ports 78 of patient support apparatus 20 (which may be a bed, a stretcher, a cot, or, in some cases, another chair), then the software package 106 associated with that chair enables patient support apparatus 20 to display the battery power of the chair on display 32 (or 32a). Further, the software package allows the patient support apparatus 20 to display on display 32 or 32a the status of the chairs brake, the height of the seat portion of the chair, the angle of the chair's footrest, the angle of the seat, and the Fowler angle of the chair. Still further, the software package 106 allows user interface 50 of patient support apparatus 20 to both display and control the following two features of the chair: the patient controls lock (which prevents the patient from using certain controls on the chair), and the exit alarm (which provides an alert if the patient exits from the chair). It will be understood that this specific list of features of the chair that are controllable and/or displayable via user interface 50 of patient support apparatus 20 is merely an illustrative list, and that other features may be added and/or substituted for the ones listed. Similarly, other features may be added and/or substituted for all of the remaining external devices 60 listed in tables 150a and 150b. Still other external devices 60 may also be added to tables 150a and 150b.

In some embodiments, the external device 60 is an application executing on a server of local area network 66. For example, in some situations, a healthcare facility may include one or more applications that aggregate data from various medical devices, electronic medical records, work flow schedules, admission and discharge records, etc. When such applications are used, patient support apparatus 20 is configured to download a software package 106 that enables controller 58a to access and receive all or a user-selected portion of the aggregated data from the software application via WiFi module 62a. The user-selected data is then displayable on display 32 (or 32a) of patient support apparatus 20.

In some modified embodiments of patient support apparatus 20, connectivity node 54a also includes an additional port (not shown) dedicated for communicating with a powered mattress. That is, the dedicated port receives a cable that is coupled to a powered mattress. When the cable is coupled to the additional port, user interface 50 of patient support apparatus 20 is able to control and display various features of the powered mattress. Unlike external devices 60, however, the powered mattress is product sold by the entity that manufactures patient support apparatus 20, and therefore patient support apparatus 20 is sold with software that communicates with the powered mattress when patient support apparatus 20 is originally sold. Patient support apparatus 20 therefore does not need to download a software package to communicate with the powered mattress. However, in some embodiments, controller 58a is configured to check to see if a more recent version exists of the software used to communicate with the powered mattress. Controller 58a does this in the same manner discussed above, i.e. by sending a request to local server 70 to retrieve and/or check to see if updated software for communicating with the powered mattress exists.

In some further modified embodiments of patient support apparatus 20, connectivity node 54a is configured to communicate with a powered mattress 60 that is manufactured by entities other than the entity that manufactures patient support apparatus 20. In these further modified embodiments, the powered mattress couples to one of ports 78 and communicates with patient support apparatus 20 using a corresponding software package 106.

Regardless of whether modified patient support apparatus 20 includes an additional port dedicated for communicating with a commonly-manufactured powered mattress, or communicates via a port 78 with a powered mattress manufactured by the same entity as patient support apparatus, user interface 50 is enabled to control and view various aspects of the powered mattress, such as, but not limited to, the inflation pressure of various zones of the mattress, therapies provided by the powered mattress, patient parameters sensed by the mattress, etc. In some embodiments, the powered mattress is any one of the mattresses sold under the brand names Isolibrium and/or XPRT by Stryker Corporation of Kalamazoo, Mich., and may include any one or more of the features described in commonly assigned U.S. patent application Ser. No. 13/836,813 filed Mar. 15, 2013 by inventors Patrick Lafleche et al. and entitled INFLATABLE MATTRESS AND CONTROL METHODS and/or commonly assigned U.S. patent application Ser. No. 14/308,131 filed Jun. 18, 2014 by inventors Patrick Lafleche et al. and entitled PATIENT SUPPORT COVER, the complete disclosures of both of which are incorporated herein by reference. In still other embodiments, still other types of mattresses may be used.

Although external devices 60 have been primarily described herein as communicating with ports 78 of patient support apparatus 20 via a cable or wire, it will be understood that patient support apparatus 20 can be modified to permit wireless communication with such external devices 60. Still further, in some embodiments, patient support apparatus 20 is modified to communicate with one or more external devices 60 via a wired connection and one or more other devices 60 via a wireless connection. In some instances, the software package 106 utilized by patient support apparatus 20 for communicating with a particular device 60 is different, depending upon whether the external device 60 is capable of wireless communication or not. Information about the wireless communication abilities of the external device 60 is stored in an initial wireless communication structure comparable to initial communication structure 80, and controller 58a uses that information to determine what software package 106 to download in order to communicate with that particular external device 60.

It will be understood that the communication principles disclosed herein regarding patient support apparatus 20 may be extended to other devices that are not patient support apparatuses. For example, the communication principles of patient support apparatus 20 disclosed herein may be applied to an electronic IV pole or other type of medical equipment support. One such suitable equipment support is disclosed in commonly assigned U.S. patent application Ser. No. 15/422,979 filed by inventors Childs et al. and entitled AN ACCESSORY SUPPORT AND COUPLING SYSTEMS FOR AN ACCESSORY SUPPORT, the complete disclosure of which is incorporated herein by reference. By applying the communication principles disclosed herein to a medical equipment support, it is possible for one or more external devices 60 to be coupled to the medical equipment support and utilize a user interface of the medical equipment support for displaying their data and/or allowing themselves to be controlled via the user interface of the medical equipment support. In this manner, the equipment support is able to support multiple pieces of medical equipment, yet provide a unified user interface for controlling and viewing the data from the multiple pieces of medical equipment that are supported on the support.

When the communication principles disclosed herein are incorporated into an equipment support, one or more patient support apparatuses 20 may function as an external device 60 with respect to the equipment support. In this manner, the data from the patient support apparatus 20 is displayable on a display of the equipment support, and one or more functions of the patient support apparatus 20 are controllable via a user interface of the equipment support. FIG. 14 illustrates a table 152 showing one example of the features of a patient support apparatus that are displayable on a user interface of an equipment support when the patient support apparatus 20 is coupled to a port (comparable to port 78) of the equipment support. The features are identified in a second column 144, followed by a third column 146 showing the units of measure for the corresponding features and a fourth column 148 indicating whether the feature is displayable and/or controllable via the user interface of the equipment support. Although FIG. 14 illustrates the patient support apparatus 20 as all being only displayable on the user interface of the equipment support (column 148), it will be understood that any one or more of these features or functions can be controllable via the user interface of the equipment support.

Although table 152 only lists a patient support apparatus, it will be understood that the medical equipment support can control and/or display data from other external devices in addition to, or in lieu of, patient support apparatuses. In some embodiments, the equipment support apparatus is adapted to communicate with any of the external devices 60 discussed above with respect to patient support apparatus 20, such as, but not limited to, those identified in tables 150a and 150b.

Still further, in some modified embodiments of patient support apparatus 20, patient support apparatus 20 is modified to communicate with a medical equipment support via one or more ports 78. When so modified, patient support apparatus 20 uses one or more software packages 106 to enable its user interface 50 to control and/or display the data from any of the pieces of medical equipment that are supported on the equipment support.

It will be understood that in any of the embodiments of the patient support apparatuses and/or medical equipment supports discussed above, the display(s) and/or controls incorporated into the devices 60 coupled to the patient support apparatus 20 or to the equipment support are not changed or otherwise rendered non-functional. For example, when an external device 60 is coupled to a patient support apparatus 20 and user interface 50 of patient support apparatus 20 shows data from external device 60 and/or allows external device 60 to be controlled thereby, any user interface that is integrated into the external device 60 itself remains functional. The user can therefore still control the external device 60 using the user interface of the external device 60 (if device 60 includes one), and/or view information regarding the external device 60 using the display of the external device 60 (if device 60 includes a display). The coupling of the external device 60 to patient support apparatus 20 (or an equipment support) therefore does not decrease any functionality of the external device 60 and its components, but instead adds an additional user interface to the device that unites the functionality of two or more user interfaces (patient support apparatus 20 and the external device 60) into a common user interface.

Various additional alterations and changes beyond those described above can be made to the above-described embodiments without departing from the spirit and broader aspects of the disclosure as defined in the appended claims, which are to be interpreted in accordance with the principles of patent law including the doctrine of equivalents. This disclosure is presented for illustrative purposes and should not be interpreted as an exhaustive description of all embodiments of the disclosure or to limit the scope of the claims to the specific elements illustrated or described in connection with these embodiments. For example, and without limitation, any individual element(s) of the described disclosure may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present disclosure is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A patient support apparatus comprising:
a support surface adapted to support a patient;
a first user interface mounted to the patient support apparatus and including a first display and a control for controlling movement of a first component of the patient support apparatus;
a port for communicating with a thermal therapy device adapted to pump temperature controlled fluid to thermal pad wrapped around a portion of the patient's body, the thermal therapy device including a second user interface including a second display adapted to display data from the thermal therapy device; and
a control system attached to the patient support apparatus, the control system in communication with the first user interface and the port, the control system adapted to initially receive an identifier from the thermal therapy device using a first communication protocol, and to subsequently communicate with the thermal therapy device using a second communication protocol different from the first communication protocol, the control system further adapted to move the first component in response to the control being activated by a user and to display a consolidated screen on the first display including both data from the thermal therapy device and a display control adapted to cause, when activated, the first display to display data from a second component of the patient support apparatus; wherein the data from the thermal therapy device includes at least one of the following: a patient target temperature, a measured patient temperature, a fluid temperature of the temperature controlled fluid, or a flow rate of the temperature controlled fluid.

2. The patient support apparatus of claim 1 wherein the control system is further adapted to receive a device type identifier when the thermal therapy device is coupled to the port; to select a software module based on the identifier; and to use the selected software module for communicating with and controlling the coupled thermal therapy device.

3. The patient support apparatus of claim 2 wherein the selected software module allows the first user interface to display a thermal therapy device control on the consolidated screen adapted to control an aspect of the thermal therapy device.

4. The patient support apparatus of claim 2 wherein the control system is further adapted to automatically check to see if a later version exists for the selected software module by communicating with a network server, and to automatically download the later version from the network server if the later version exists.

5. The patient support apparatus of claim 2 wherein the selected software module is transferred to a memory of the patient support apparatus from a location off-board the patient support apparatus.

6. The patient support apparatus of claim 1 wherein the first communication protocol is a 1-wire communication protocol.

7. The patient support apparatus of claim 6 wherein the control system is further adapted to use the identifier received from the thermal therapy device using the first communication protocol to determine the second communication protocol.

8. The patient support apparatus of claim 6 wherein the control system is further adapted to receive a device property from the thermal therapy device using the first communication protocol, wherein the device property informs the control system whether or not the thermal therapy device can be controlled via the first user interface.

9. A patient support apparatus comprising:
a support surface adapted to support a patient;
a first user interface mounted to the patient support apparatus and including a first display and a control for controlling movement of a component of the patient support apparatus;
a scale system adapted to measure a weight of the patient;
a first port for communicating with a thermal therapy device adapted to pump temperature controlled fluid to thermal pad wrapped around a portion of the patient's body, the thermal therapy device including a second user interface including a second display adapted to display data from the thermal therapy device;
a second port for communicating with a mattress positioned on the support surface; and
a control system attached to the patient support apparatus, the control system in communication with the first user interface, the scale system, and the first and second ports, the control system adapted to display on the first display a screen for controlling the scale system and to move the component in response to the control being activated by a user, the control system further adapted to initially receive an identifier from the thermal therapy device using a first communication protocol, and to subsequently communicate with the thermal therapy device using a second communication protocol different from the first communication protocol, the control system further adapted to display first, second, and third icons on the first display when the thermal therapy device and mattress are coupled to the first and second ports, respectively, wherein the control system is further adapted to display first data from the thermal therapy device on the first display when the first icon is selected, to display second data from the mattress on the first display when the second icon is selected, and to display scale data from the scale system on the first display when the third icon is selected.

10. The patient support apparatus of claim 9 wherein the thermal therapy device and the mattress are manufactured by an entity different from a manufacturer of the patient support apparatus.

11. The patient support apparatus of claim 9 wherein the control system is adapted to automatically determine, when the thermal therapy device is initially coupled to the first port, if first software is stored in a memory of the patient support apparatus for allowing the first display to display the first data, and if the first software is not stored in the memory of the patient support apparatus, the control system is configured to automatically request the first software from a server on a network of a healthcare facility.

12. The patient support apparatus of claim 1 wherein the patient support apparatus is a bed comprising:
a plurality of lifts adapted to raise and lower a height of the support surface;
a plurality of siderails adapted to be moved between raised and lowered positions;
an exit detection system adapted to issue an exit alert when the patient exits from the support surface;
a first wireless transceiver adapted to wirelessly communicate with an access point of a local area network; and a second wireless transceiver adapted to wirelessly communicate with a nurse call system.

13. The patient support apparatus of claim 9 wherein the control system is further configured to display at least one of the following on the first display of the first user interface when the first icon is selected: a patient target temperature received from the thermal therapy device, a measured patient temperature received from the thermal therapy device, or a fluid temperature received from the thermal therapy device of the temperature controlled fluid.

14. The patient support apparatus of claim 9 wherein the first data includes at least one of the following: a patient target temperature, a measured patient temperature, a fluid temperature of the temperature controlled fluid, or a flow rate of the temperature controlled fluid.

15. The patient support apparatus of claim 9 wherein the first communication protocol is a 1-wire communication protocol.

16. The patient support apparatus of claim 15 wherein the control system is further adapted to use the identifier received from the thermal therapy device using the first communication protocol to determine the second communication protocol.

17. The patient support apparatus of claim 15 wherein the control system is further adapted to receive a device property from the thermal therapy device using the first communication protocol, wherein the device property informs the control system whether or not the thermal therapy device can be controlled via the first user interface.

\* \* \* \* \*